United States Patent [19]
Gotschlich

[11] Patent Number: 5,705,367
[45] Date of Patent: Jan. 6, 1998

[54] GLYCOSYLTRANSFERASES FOR BIOSYNTHESIS OF OLIGOSACCHARIDES, AND GENES ENCODING THEM

[75] Inventor: Emil C. Gotschlich, New York, N.Y.

[73] Assignee: The Rockefeller University, New York, N.Y.

[21] Appl. No.: 683,426

[22] Filed: Jul. 18, 1996

Related U.S. Application Data

[62] Division of Ser. No. 312,387, Sep. 26, 1994, Pat. No. 5,545,553.

[51] Int. Cl.$^6$ .............................. C12P 19/18; C12N 9/10
[52] U.S. Cl. .............................................. 435/97; 435/193
[58] Field of Search ...................................... 435/97, 193

[56] References Cited

U.S. PATENT DOCUMENTS 5,180,674  1/1993  Roth ........................................ 435/288

FOREIGN PATENT DOCUMENTS

WO 93/13198  7/1993  WIPO.

OTHER PUBLICATIONS

Sandlin and Stein, 1994, J. Bacteriol. 176:2930–37.
Gibson et al., 1993, J. Bacteriol. 175:2702–12.
Jennings et al., 1993, Molec. Microbiol. 19:361–69.
Robertson et al., 1993, Molec. Microbiol. 8:891–901.
van Putten, 1993, EMBO J. 12:4043–51.
Verheul et al., 1993, Microbiol. Rev. 57:34–49.
Kerwood et al., 1992, Biochemistry 31 : 12760–68.
Knight et al., 1992, Molec. Microbiol. 6:1565–73.
Mandrell, 1992, Infect. Immunol. 60:3017–20.
Pradel et al., 1992, J. Bacteriol. 174:4736–45.
John et al., 1991, J. Biol. Chem. 266:19303–11.
Jonsson et al., 1991, EMBO J. 10:477–88.
Mandrell et al., 1991, J. Bacteriol. 173:2823–32.
Schneider et al., 1991, J. Exp. Med. 174:1601–05.
Tsai and Civin, 1991, Infect. Immun. 59:3604–09.
Mandrell et al., 1990, J. Exp. Med. 171:1649–64.
Parsons et al., 1989, Microb. Pathog. 7:63–72.
Dudas and Apicella, 1988, Infect. Immun. 56:499–504.
Mandrell et al., 1988, J. Exp. Med. 168:107–26.
Schneider et al., 1988, Infect. Immun. 56:942–46.
Apicella et al., 1987, Infect. Immun. 55:1755–61.
Webster et al., 1983, J. Biol. Chem. 258:10637–41.
Danaher et al. (1995) Genetic Basis of *Neisseria gonorrhoeae* Lipooligosaccharide Antigenic Variation. J. Bact. 177(24): 7275–7279.
Cope et al. (1991) Molecular Cloning of a Gene Involved in Lipooligosaccharide Biosynthesis and Virulence Expression by *Haemophilus influenzae* Type B. Mol. Microbiol. 5(5): 1113–1124.
High et al. (1993) The role of a Repetitive DNA Motif (5'–CAAT–3') in the Variable Expression of the *Haemophilus influenzae* Lipopolysaccharide Epitope Alpha–Gal. (1,4)Beta–Gal Mol. Microbiol. 9(6): 1275–1282.
Zhou et al. (1994) Lipooligosaccharide Biosynthesis in *Neisseria gonorrhoeae*: Cloning, Identification and Characterization of the Alpha 1,5 Heptosyltransferase I Gene (rfaC). Mol. Microbiol. 14(4): 609–618.

*Primary Examiner*—Robert A. Wax
*Assistant Examiner*—Lisa J. Hobbs
*Attorney, Agent, or Firm*—Klauber & Jackson

[57] ABSTRACT

The present invention is directed to nucleic acids encoding glycosyltransferases, the proteins encoded thereby, and to methods for synthesizing oligosaccharides using the glycosyltransferases of the invention. In particular, the present application is directed to identification a glycosyltransferase locus of *Neisseria gonorrhoeae* containing five open reading frames for five different glycosyltransferases. The functionally active glycosyltransferases of the invention are characterized by catalyzing reactions such as adding Gal β→4 to GlcNAc or Glc; adding GalNAc or GlcNAc β1→3 to Gal; and adding Gal α1→4 to Gal. The glycosyltransferases of the invention are particularly suited to the synthesis of the oligosaccharides Galβ1→4GlcNAcβ1→3Galβ1→4Glc (a mimic of lacto-N-neotetraose), GalNAcβ1→3Galβ1→4GlcNAcβ1→3Galβ1→4Glcβ1→4 (a mimic ganglioside), and Galα1→4Galβ1→4Glcβ1→4Hep→R (a mimic of the saccharide portion of globo-glycolipids).

3 Claims, 11 Drawing Sheets

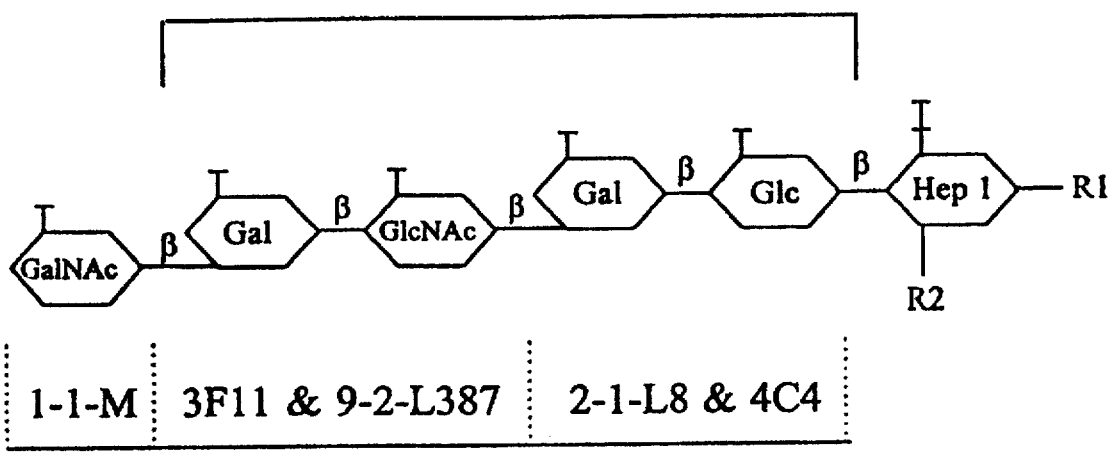
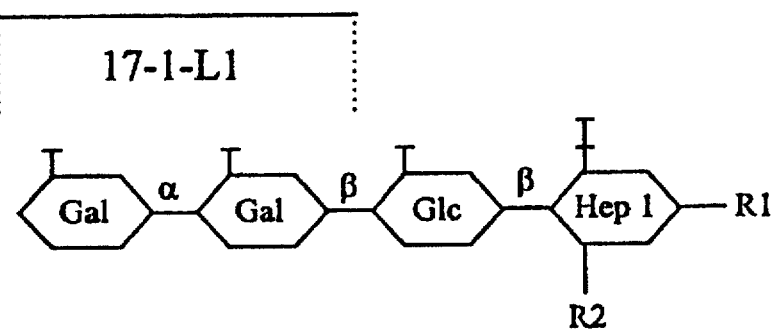
FIG. 1

Comparison of lgtA and lgtD

```
lgtA     1 LQPLVSVLICAYNVEKYFAQSLAAVVNQTWRNLDILILIVDDGSTDGTLAIA    50
           ||||||||||||||| ||||||||| |||||||||||||||||||| ||||
lgtD     1 LQPLVSVLICAYNAEKYFAQSLAAVVGQTWRNLDILILIVDDGSTDGTPAIA    50 lgtA    51 KDFQKRDSRIKILAQAQNSGLIPSLNIGLDELAKSGGGGGEYIARTDADD    100
              ||||| |  |  |           ||||||||||||    ||||||||||
lgtD    51 RHFQEQDGRIRIISNPRNLGFIASLNIGLDELAKS..GGGEYIARTDADD     98 lgtA   101 IASPGWIEKIVGEMEKDRSIIAMGAWLEVLSEEKDGNRLARHHKHGKIWK    150
           ||||||||||||||||||||||||||||||||| :  :
lgtD    99 IASPGWIEKIVGEMEKDRSIIAMGAWLEVLSEENNKSVLAAIARNGAIWD    148 lgtA   151 KPTRHEDIAAFFPFGNPIHNNTMIMRRSVIDGGLRYDTERDWAEDYQFWY    200
           ||||||||| :   |:||||||||||||||||||||||    ||| |||
lgtD   149 KPTRHEDIVAVFPFGNPIHNNTMIMRRSVIDGGLRFDPAYIHAEDYKFWY    198
```

FIG. 3A

```
lgtA 201 DVSKLGRLAYYPEALVKYRLHANQVSSKHSVRQHEIAQGIQKTARNDFLQ 250
             : ::||||||||||||||||:|::::::|:::|:||::::
lgtD 199 EAGKLGRLAYYPEALVKYRFHQDQTSSKYNLQQRRTAWKIKEEIRAGYWK 248 lgtA 251 SMGFKTRFDSLEYRQTKAAAYELPEKDLPEEDFFERARRFLYQCFKRTDTP 300
             : ::||::|:|::::|::|:|:::|:||
lgtD 249 AAGIAVGADCLNYGLLKSTAYALYEKALSGQDIGCLRLFLYEYFLSLEKY 298 lgtA 301 PSGAWLDFAADGRMRRLFTLRQYFGILYRLIKNRR 335
             ::|||:|:|:|:::|||:|||:::
lgtD 299 SLTDLLDFLTDRVMRKLFAAPQYRKILKKMLRPWK 333
```

FIG. 3B

Comparison of lgtB and lgtE

```
lgtB   1 MQNHVISLASAAERRAHIADTFGSRGIPFQFFDALMPSERLEQAMAELVP 50
         ||||||||||||||||||||||||||||||||||||||||||||||||||
lgtE   1 MQNHVISLASAAERRAHIADTFGSRGIPFQFFDALMPSERLEQAMAELVP 50 lgtB  51 GLSAHLYLSGVEKACFMSHAVLWEQALDEGLPYIAVFEDDVLLGEGAEQF 100
         ||:||:||||||||||||||||||||||||||||||||||||||||||||
lgtE  51 GLSAHPYLSGVEKACFMSHAVLWEQALDEGLPYIAVFEDDVLLGEGAEQF 100 lgtB 101 LAEDTWLQERFDPDSAFVVRLETMFMHVLTSPSGVADYGGRAFPLLESEH 150
         ||||||||:||| :||:|||||||| :   :  :     :   ||||||
lgtE 101 LAEDTWLEERFDKDSAFIVRLETMFAKVIVRPDKVLNYENRSFPLLESEH 150 lgtB 151 CGTAGYIISRKAMRFFLDRFAVLPPERLHPVDLMMFGNPDDREGMPVCQL 200
         |||||||||||:||||||||||||||||:|||||||   |  :|||:|:
lgtE 151 CGTAGYIISREAMRFFLDRFAVLPPERIKAVDLMMFTYFFDKEGMPVYQV 200
```

FIG. 4A

```
lgtB 201 NPALCAQELHYAKFHDQNSALGSLIEHDRRLNRKQQRRDSPANTFKHRLI 250
             :||||||||||||  :|  ||| ||:|
lgtE 201 SPALCTQELHYAKFLSQNSMLGSDLEKD......REQGRRHRRSLKVMFDLK 246 lgtB 251 RALTKIGREREKRRKRR......EQTIGKIIVPFQ 279
         ||| ::||||:| ::    :: ::|  :
lgtE 247 RALGKFGREKKKKRMERQRQAELELEKVYGRRVILFK 280
```

FIG. 4B

Comparison of rfaI and lgtC

```
rfaI   29 LDIAYGTDKNFLFGCGISIASILKYNEGSRLCFHIFTDYFGDDDRKYFDA  78
          :   ::    :   :: :   ::  :::::: :::
lgtC    1 MDIVFAADDNYAAYLCVAAKSVEAAHPDTEIRFHVLDAGISEENRAAVAA  50 rfaI   79 LALQYKTRIKIYLINGDRLRSLP.STKNWTHAIYFRFVIADYFINKAPKV 127
          :  :: ::: ::   :: ::    ::  ::   :: :::
lgtC   51 .NLRGGGNIRFIDVNPEDFAGFPLNIRHISITTYARLKLGEY.IADCDKV  98 rfaI  128 LYLDADIICQGTIEPLINFSFPDDKVAMVV...TEGQADWEKRAHSLGV 174
          :::: :: ::: :::: : : ::  ::                 :::
lgtC   99 LYLDTDVLVRDGLKPLWDTDLGGNWVGACIDLFVERQEGYKQK....IGM 144 rfaI  175 AGIAKGYFNSGFLLINTAQWAAQQVSARAIAMLNEPEIIKKITHPDQDVL 224
          :  :: :::  :  ::  :                      :: ::
lgtC  145 AD.GEYYFNAGVLLIINLKKWRRHDIFKMSCEWVEQYKDVMQ..YQDQDIL 191
```

FIG. 5A

```
rfaI 225 NMLLADKLIFADIKYNTQFSLNYQLKESFINPVTNDTIFI............  264
            :.::: :::  :  .:  .:  :   :.:::
lgtC 192 NGLFKGGVCYANSRFNF.MPTNYAFMANGFASRHTDPLYLDRTNTAMPVA  240 rfaI 265 ..HYIGPTKPWHDWAWDYPVSQAFMEAKNASPWKNTALLKPNNSNQLRYS  312
           :.:.:  ::|||  : ::|:|  :    :.::
lgtC 241 VSHYCGSAKPWH...RDCTVWGAERFTELAGSL..TTVPEEWRGKLAVPP  285 rfaI 313 AKHMLKKHRYLKGFSNYLFYFI  334
         .: .::  :.:    :
lgtC 286 TKCML..QRWRKKLSARFLRKI  305
```

FIG. 5B

GLYCOSYLTRANSFERASES FOR BIOSYNTHESIS OF OLIGOSACCHARIDES, AND GENES ENCODING THEM

This application is a Division, of application Ser. No. 08/312,387 filed Sep. 26, 1994 now U.S. Pat. No. 5,545,553.

The research leading to the present invention was supported in part with funds from grant number AI-10615 from the Public Health Service. Accordingly, the Government may have certain rights in the invention.

FIELD OF THE INVENTION

The present invention relates to glycosyltransferases useful for biosynthesis of oligosaccharides, genes encoding such glycosyltransferases and recombinant methods of producing the enzymes, and the oligosaccharides produced thereby.

BACKGROUND OF THE INVENTION

Neisseria and Lipo-oligosaccharide (LOS)

While Neisseria species commonly colonize many mammalian hosts, human beings are the only species subject to invasive disease by members of this species. *Neisseria meningitidis* is the etiologic agent for septicemia and meningitis that may occur in epidemic form. *Neisseria gonorrhoeae* is the causative agent of gonorrhea and its manifold complications. These organisms, particularly the gonococcus, have proved remarkably adept at varying the antigenic array of their surface-exposed molecules, notably their adhesive pili and opacity-related (opa) proteins. The genetic mechanisms for the variation of pilus (Meyer et al., 1982, Cell 30:45; Haas and Meyer, 1986, Cell 44: 107; Koomey et al., 1987, Genetics 117:391; Swanson and Koomey, 1989, American Society for Microbiology, Washington, 743–761) and opa protein (Stern et al., 1986, Cell 47:61; Meyer et al., 1990, Ann. Rev. Microbiol. 44:451; Bhat et al., 1991, Molec. Microbiol. 5: 1889) expression are in the main well understood. Like other Gram-negative bacteria the Neisseria ssp. carry LPS in the external leaflet of their outer membranes (Johnston and Gotschlich, 1974, J. Bacteriol. 119;250). In contrast to the high molecular weight LPS molecules with repeating O-chains seen in many enteric bacteria, the LPS of Neisseria ssp. is of modest size and therefore is often referred to as lipooligosaccharide or LOS. Although the molecular size of the LOS is similar to that seen in rough LPS mutants of Salmonella ssp., this substance has considerable antigenic diversity. In the case of the meningococcus, a serological typing scheme has been developed that separates strains into 12 immunotypes (Zollinger and Mandrell, 1977, Infect. Immun. 18:424; Zollinger and Mandrell, 1980, Infect. Immun. 28:451). A remarkably complete understanding of the structure of meningococcal LPS (recently reviewed (Verheul et al., 1993, Microbiol. Rev. 57:34) has resulted from the studies of Jennings and his colleagues (Jennings et al., 1983, Carbohyd. Res. 121:233; Michon et al., 1990, J. Biol. Chem. 265:7243; Gamian et al., 1992, J. Biol. Chem. 267:922; Pavliak et al., 1993, J. Biol. Chem. 268: 14146). In the case of *Neisseria gonorrhoeae*, antigenic variability is so pronounced that a serological classification scheme has proved elusive. In part this is due to the heterogeneity of LOS synthesized by a particular strain; LOS preparations frequently contain several closely spaced bands by SDS-PAGE (Mandrell et al., 1986, Infect. Immun. 54:63). Further, studies using monoclonal antibodies indicate, that gonococci are able to change the serological characteristics of the LOS they express and that this antigenic variation occurs at a frequency of $10^{-2}$ to $10^{-3}$, indicating that some genetic mechanism must exist to achieve these high frequency variations (Schneider et al., 1988, Infect. Immun. 56:942; Apicella et al., 1987, Infect. Immun. 55: 1755). Because of the molecular heterogeneity and antigenic variation of the LOS produced by gonococci the determination of the structural chemistry of this antigen has proved to be a difficult problem, and definitive information based on very sophisticated analyses has only recently become available (Yamasaki et al, 1991, Biochemistry 30:10566; Kerwood et al., 1992, Biochemistry 31:12760; John et al., 1991, J. Biol. Chem. 266:19303; Gibson et al., 1993, J. Bacteriol. 175:2702). These are summarized in FIG. 1. Of particular interest is the presence of the tetrasaccharide Gal$\beta$1→4GlcNAc$\beta$1→3Gal$\beta$1→4Glc$\beta$1→4, which is a perfect mimic of lacto-N-neotetraose of the sphingolipid paragloboside (Mandrell et al., 1988, J. Exp. Med. 168: 107; Tsai and Civin, 1991, Infect. Immun. 59:3604). In LOS this tetrasaccharide frequently bears an additional N-acetyl galactosamine residue (GalNAc$\beta$1→3Gal$\beta$1→4GlcNAc$\beta$1→3Gal$\beta$1→4Glc$\beta$1→4), and then mimics gangliosides. In some strains of gonococci an alternative side chain is found which has the structure Gal$\alpha$1→4Gal$\beta$1→4Glc$\beta$1→4Hep→R (John et al., 1991, J. Biol. Chem. 266:19303). This is a mimic of the saccharide portion of globo-glycolipids (Mandrell, 1992, Infect. Immun. 60:3017), and is the structure characteristically found in *Neisseria meningitidis* immunotype L1.

The LOS molecules have a number of biological activities. They are potent endotoxic molecules believed to be the toxin responsible for adrenal cortical necrosis seen in severe meningococcal disease. They serve as the target antigen for much of the bactericidal activity present in normal or convalescent human sera (Rice et al., 1980, J. Immunol. 124:2105). Gonococci possess a very unusual sialyl transferase activity which is able to use externally supplied CMP-NANA and add N-acetyl neuraminic acid to the LOS on the surface of the organism (Nairn et al., 1988, J. Gen. Microbiol. 134:3295; Parsons et al., 1989, Microb. Pathog. 7:63; Mandrell et al., 1990, J. Exp. Med. 171:1649). Group B and C meningococci, have the capacity to synthesize CMP-NANA, and frequently sialylate their LOS without requiring exogenous CMP-NANA (Mandrell et al., 1991, J. Bacteriol. 173:2823). In *Neisseria meningitidis* strain 6275 immunotype L3, the sialic acid unit is linked $\alpha$2→3 to the terminal Gal residue of the lacto-N-neotetraose (Yamasaki et al., 1993, J. Bacteriol. 175:4565). The levels of CMP-NANA found in various host environments is sufficient to support this reaction (Apicella et al., 1990, J. Infect. Dis. 162:506). The sialylation of the LOS causes gonococci to become resistant to the antibody-complement dependent bactericidal effect of serum (Parsons et al., 1989, Microb. Pathog. 7:63). The resistance is not only to the bactericidal effect mediated by antibodies to LOS, but to other surface antigens as well (Wetzler et al., 1992, Infect. Immun. 60:39). van Putten has demonstrated that exposure of gonococci to CMP-NANA markedly reduces their ability to invade epithelial cells in tissue culture (Van Putten, 1993, EMBO J. 12:4043). These findings strongly suggest that the ability of gonococci to vary the chemical nature of the LOS provides them with the ability to cope with different host environments (Mandrell and Apicella, 1993, Immunobiology 187:382).

Perhaps most telling, it has been found that LOS variation is selected in vivo in infections of human beings. A well characterized gonococcal laboratory strain MS11$_{mk}$ variant A was used to inoculate volunteers (Swanson et al., 1988, J. Exp. Med. 168:2121). In the two infected individuals over a period of 4 to 6 days the population of gonococci recovered in their urine increasingly shifted to two variants that expressed antigenically different LOS (Schneider et al., 1991, J. Exp. Med. 174:1601). A structural analysis revealed that the inoculated variant A produced a truncated LOS containing only the β-lactosyl group linked to Hep1, while one of the new variants (variant C) produced a complete LOS (Kerwood et al., 1992, Biochemistry 31:12760). This suggests that the addition of the additional sugars GalNAcβ1→3Galβ1→4GlcNAcβ1→3 is likely to be under control of a phase variation mechanism.

Little information on the genetics of LOS synthesis in Neisseria is available. A major advance has been the creation (Dudas and Apicella, 1988, Infect. Immun. 56:499) and biochemical characterization (John et al., 1991, J. Biol. Chem. 266:19303) of five pyocin mutants of gonococcal strain 1291, dubbed 1291a-e. Immunological and biochemical data have shown that 1291a, 1291c, 1291d and 1291e produce LOS with sequential shortening of the lacto-N-neotetraose chain, with mutant 1291e lacking the glucose substitution on the heptose. Mutant 1291b synthesizes the alternative LOS structure Galα1→4Galβ1→4Glc (see FIG. 1). Only the genetic basis of the 1291e mutant is now defined. It is a mutation of phosphoglucomutase (pgm), which precludes the synthesis of UDP-glucose, and hence the addition of the first residue of the lacto-N-neotetraose unit (Zhou et al., 1994, J. Biol. Chem. 269:11162; Sandlin and Stein, 1994, J. Bacteriol. 176:2930). It also has been shown that gale mutants of meningococcus or gonococcus produce truncated LOS in keeping with the inability to synthesize UDP-galactose (Robertson et al., 1993, Molec. Microbiol. 8:891; Jennings et al., 1993, Molec. Microbiol. 10:361).

Biosynthesis of Oligosaccharides

Oligosaccharides are polymers of varying number of residues, linkages, and subunits. The basic subunit is a carbohydrate monosaccharide or sugar, such as mannose, glucose, galactose, N-acetylglucosamine, N-acetylgalactosamine, and the like. The number of different possible stereoisomeric oligosaccharide chains is enormous.

Oligosaccharides and polysaccharides play an important role in protein function and activity, by serving as half-life modulators, and, in some instances, by providing structure. As pointed out above, oligosaccharides are critical to the antigenic variability, and hence immune evasion, of Neisseria, especially gonococcus.

Numerous classical techniques for the synthesis of carbohydrates have been developed, but these techniques suffer the difficulty of requiring selective protection and deprotection. Organic synthesis of oligosaccharides is further hampered by the lability of may glycosidic bonds, difficulties in achieving regioselective sugar coupling, and generally low synthetic yields. In short, unlike the experience with peptide synthesis, traditional synthetic organic chemistry cannot provide for quantitative, reliable synthesis of even fairly simple oligosaccharides.

Recent advances in oligosaccharide synthesis have occurred with the isolation of glycosyltransferases. These enzymes can be used in vitro to prepare oligosaccharides and polysaccharides (see, e.g., Roth, U.S. Pat. No. 5,180, 674, issued Jan. 19, 1993). The advantage of biosynthesis with glycosyltransferases is that the glycosidic linkages formed by enzymes are highly stereo and regiospecific. However, each enzyme catalyzes linkage of specific sugar residues to other specific acceptor molecules, e.g., an oligosaccharide or lipid. Thus, synthesis of a desired oligosaccharide may be limited by the availability of glycosyltransferases (see, Roth, International Patent Publication No. WO 93/13198, published Jul. 8, 1993).

Another drawback of biosynthesis is that the glycosyltransferases themselves are usually present in fairly low quantities in cells. It is difficult to obtain enough of the enzyme to be commercially practicable.

Thus, there is a great need in the art for glycosyltransferases. There is a further need for genes encoding such glycosyltransferases, to provide an unlimited source of glycosyltransferases through recombinant technology.

The citation of any reference herein should not be construed as an admission that such reference is available as prior art to the instant invention.

SUMMARY OF THE INVENTION

The present invention is directed to nucleic acids encoding glycosyltransferases, the proteins encoded thereby, and to methods for synthesizing oligosaccharides using the glycosyltransferases of the invention. Accordingly, in one aspect, the invention is directed to a purified nucleic acid that is hybridizable under moderately stringent conditions to a nucleic acid corresponding to the LOS locus of Neisseria, e.g., a nucleic acid having a nucleotide sequence corresponding to or complementary to the nucleotide sequence shown in (SEQ ID NO:1). Preferably, the nucleic acid of the invention is hybridizable to a portion of the coding sequence for a gene of the LOS locus, i.e., a portion of the nucleotide sequence shown in (SEQ ID NO:1) that encodes a functionally active glycosyltransferase.

In specific embodiments, the invention relates to a nucleic acid that has a nucleotide sequence corresponding to or complementary to a portion of the nucleotide sequence shown in (SEQ ID NO:1) that encodes a functionally active glycosyltransferase. In a further aspect, the nucleic acid encodes a functionally active glycosyltransferase. In a specific embodiment, the invention is directed to a nucleic acid that has a nucleotide sequence corresponding to or complementary to the nucleotide sequence shown in (SEQ ID NO:1).

The functionally active glycosyltransferases of the invention are characterized by catalyzing a reaction selected from the group consisting of:

adding Gal β1→4 to GlcNAc or Glc;
adding GalNAc or GlcNAc β1→3 to Gal; and
adding Gal α1→4 to Gal.

Most preferably, the claimed nucleic acid encodes a functionally active glycosyltransferase. However, nucleic acids of the invention include oligonucleotides useful as primers for polymerase chain reaction (PCR) or for probes for the presence and level of transcription of a glycosyltransferase gene.

In specific embodiments, exemplified herein, the nucleic acid encodes a glycosyltransferase having an amino acid sequence of SEQ ID NO:3 or SEQ ID NO:11, SEQ ID NO:4, SEQ ID NO:5, SEQ ID NO:12 or SEQ ID NO:6 or SEQ ID NO:8.

The invention further relates to an expression vector comprising the nucleic acid encoding a glycosyltransferase of the invention operatively associated with an expression control sequence. Accordingly, the invention extends to recombinant host cell transformed with such an expression vector.

In another aspect, the invention is directed to a method for producing a glycosyltransferase comprising culturing the recombinant host cell under conditions that allow expression of the glycosyltransferase; and recovering the expressed glycosyltransferase.

In a primary aspect, the invention is directed to glycosyltransferase having an amino acid sequence of SEQ ID NO:3 or SEQ ID NO:11, SEQ ID NO:4, SEQ ID NO:5, or SEQ ID NO:12 or SEQ ID NO:6 or SEQ ID NO:8 or a functionally active fragment thereof. The invention further contemplates a composition comprising a glycosyltransferase conjugated to a solid phase support, wherein the glycosyltransferase is selected from the group consisting of a glycosyltransferase having an amino acid sequence of SEQ ID NO:3 or SEQ ID NO:11 or a functionally active fragment thereof; a glycosyltransferase having an amino acid sequence of SEQ ID NO:8, or a functionally active fragment thereof; a glycosyltransferase having an amino acid sequence of SEQ ID NO:4, or a functionally active fragment thereof; and a glycosyltransferase having an amino acid sequence of SEQ ID NO:5 or SEQ ID NO:12, or a functionally active fragment thereof; and a glycosyltransferase having an amino acid sequence of SEQ ID NO:6, or a functionally active fragment thereof.

Having provided novel glycosyltransferases, and genes encoding the same, the invention accordingly further provides methods for preparing oligosaccharides, e.g., two or more saccharides. In specific embodiments, the invention relates to a method for adding GalNAc or GlcNAc $\beta 1 \rightarrow 3$ to Gal, comprising contacting a reaction mixture comprising an activated GalNAc or GlcNAc to an acceptor moiety comprising a Gal residue in the presence of the glycosyltransferase having an amino acid sequence of SEQ ID NO:3 or SEQ ID NO:11, a method for adding Gal$\beta 1 \rightarrow 4$ to GlcNAc or Glc, comprising contacting a reaction mixture comprising an activated Gal to an acceptor moiety comprising a GlcNAc or Glc residue in the presence of the glycosyltransferase having an amino acid sequence of SEQ ID NO:8, a method for adding Gal $\alpha 1 \rightarrow 4$ to Gal, comprising contacting a reaction mixture comprising an activated Gal to an acceptor moiety comprising a Gal residue in the presence of the glycosyltransferase having an amino acid sequence of SEQ ID NO:4; a method for adding GalNAc or GlcNAc $\beta 1 \rightarrow 3$ to Gal, comprising contacting a reaction mixture comprising an activated GalNAc or GlcNAc to an acceptor moiety comprising a Gal residue in the presence of the glycosyltransferase having an amino acid sequence of SEQ ID NO:5 SEQ ID NO:12, and a method for adding Gal $\beta 1 \rightarrow 4$ to GlcNAc or Glc, comprising contacting a reaction mixture comprising an activated Gal to an acceptor moiety comprising a GlcNAc or Glc residue in the presence of the glycosyltransferase having an amino acid sequence of SEQ ID NO:6.

In a preferred embodiment, the oligosaccharides are prepared on a carrier that is non-toxic to a mammal, in particular a human, such as a lipid isoprenoid or polyisoprenoid alcohol. A specific example of such a carrier is dolichol phosphate. In a specific embodiment, the oligosaccharide is attached to the carrier via a labile bond, thus allowing for chemically removing the oligosaccharide from the lipid carrier. Alternatively, an oligosaccharide transferase can be used, e.g., to transfer the oligosaccharide from a lipid carrier to a protein. In yet another embodiment, the glycosyltransferases can be expressed in a eukaryotic expression system, to provide for glycosylation of a protein expressed in such a system.

An important advantage of the present invention is that it provides for the synthesis of oligosaccharide antigens of Neisseria independently of lipid A, which is highly toxic. Use of the natural LOS from Neisseria, while theoretically desirable for vaccine preparation, fails. The lipid A portion of LOS is a potent endotoxin, and highly toxic. Chemical treatment of the LOS, e.g., by hydrolysis, destroys the antigenicity of the oligosaccharide, leaving a useless product. Thus, it is highly desirable to have a source of Neisseria oligosaccharides attached to non-toxic lipids for vaccine preparation.

Thus, the invention provides glycosyltransferases and strategies for preparing a number of oligosaccharides, such as but not limited to, Gal$\alpha 1 \rightarrow$4Gal$\beta 1 \rightarrow$4Glc, Gal$\beta 1 \rightarrow$4GlcNAc$\beta 1 \rightarrow$3Gal$\beta 1 \rightarrow$4Glc, and GalNAc$\beta 1 \rightarrow$3Gal$\beta 1 \rightarrow$4GlcNAc$\beta 1 \rightarrow$3Gal$\beta 1 \rightarrow$4Glc.

Accordingly, it is a primary object of the invention to provide glycosyltransferases useful for the synthesis of oligosaccharides.

It is a further object of the invention to provide for the synthesis of oligosaccharides characteristic of *Neisseria meningitidis* and *N. gonorrhoeae*.

It is a further object of the invention to provide for the synthesis of oligosaccharides characteristic of mammalian oligosaccharides, including blood group core oligosaccharides.

It is still a further object of the invention to provide for vaccines having the oligosaccharide unit of LOS, but lacking lipid A.

Still a further object of the invention is to provide for synthesis of therapeutically useful oligosaccharides.

These and other objects of the present will be made clear by reference to the following Drawings and Detailed Description.

BRIEF DESCRIPTION OF THE DRAWINGS

FIG. 1: Alternative structures found in gonococcal LOS. R1 refers to the inner core region of LOS consisting of two keto-deoxy-octulosonic acid (KDO) residues. These in turn are attached to a lipid A structure. R2 in gonococci is typically GlcNAc$\beta 1 \rightarrow$2Hep$\alpha 1 \rightarrow$3. The structure in the top panel contains a tetrasaccharide identical to lacto-N-neotetraose found in paragloboside glycolipids. In many strains this tetrasaccharide bears a terminal GalNAc$\beta 1 \rightarrow$3. The lower panel shows an alternative trisaccharide structure with the terminal Gal $\alpha 1 \rightarrow$4 linked. This trisaccharide is seen in meningococci of the L1 serotype and in some gonococcal strains. The portions of the two structures recognized by the monoclonal antibodies used in this study are indicated (4C4) (Dudas and Apicella, 1988, Infect. Immun. 56:499) 3F11 (Mandrell et al., 1988, J. Exp. Med. 168–107; Yamasaki et al., 1991, Mol. Immunol. 28:1233) 1-1-M (Yamasaki et al., 1991, Mol. Immunol. 28:1233), 2-1-L8 (Kerwood et al., 1992, Biochemistry 31:12760; Schneider et al., 1991, J. Exp. Med. 174:1601; Schneider et al., 1985, Infect. Immun. 50:672) 9-2-L378 and 17-1-L1.

FIG. 3: Homology of the protein products of lgtA (SEQ ID NO:11) and lgtD (SEQ ID NO:12). The primary structure of two proteins is very similar, particularly in the first half of the sequences. The glycine residues starting at position 86 reflect the coding of the poly-G regions in the respective genes. The Bestfit program of the GCG package was used and the symbols !,:, . represent degrees of similarity based on the Dayhoff PAM-250 matrix.

FIG. 4: Homology of the protein products of lgtB and lgtE. The primary structure of two proteins is very similar, particularly in the first half of the sequences. These sequences also have significant homology to lex-1 (Cope et al., 1991, Molec. Microbiol. 5:1113) or lic2A (High et al., 1993, Molec. Microbiol. 9:1275) genes of *Haemophilus influenzae*. For meaning of symbols see FIG. 3.

FIG. 5: Homology of the protein products of rfaI and lgtC. The *E. coli* rfaI and rfaJ genes are very closely related. They serve as glucosyl transferases of two glucose residues in the LPS core region (Pradel et al., 1992, J. Bacteriol. 174:4736). The glycines at position 54–56 in lgtC are encoded by the poly-G tract. For meaning of symbols see FIG. 3.

DETAILED DESCRIPTION OF THE INVENTION

Figure 2:
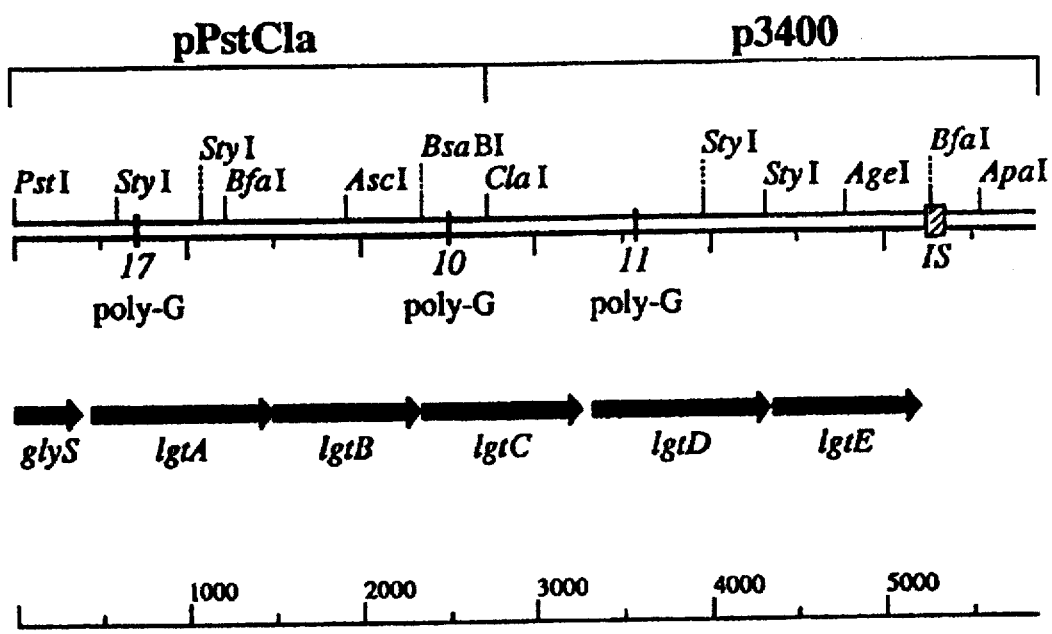
FIG. 2: Genetic map of the LOS locus based on the DNA sequence. Sequence information bp 1-2725 was obtained from plasmid pPstCla, bp 2725–5859 from plasmid p3400 (see materials and methods). IS refers to an area of the sequence that has homology to a previously reported neisserial insertion sequence IS1106 (Knight et al., 1992, Molec. Microbiol. 6:1565). The positions of the reading frames of lgtA-E are indicated. Three tracts of poly-G Were found in lgtA (17 bp), lgtC (10 bp) and lgtD (11 bp) and are indicated by vertical black bars.

As disclosed above, the present invention provides five novel glycosyltransferases, genes encoding the glycosyltransferases, and methods for biosynthesis of oligosaccharides using such glycosyltransferases. The glycosyl transferases of the invention can be used for in vitro biosynthesis of various oligosaccharides, such as the core oligosaccharide of the human blood group antigens, i.e., lacto-N-neotetraose.

Cloning and expression of glycosyltransferases of the invention can be accomplished using standard techniques, as disclosed herein. Such glycosyl transferases are useful for biosynthesis of oligosaccharides in vitro, or alternatively genes encoding such glycosyltransferases can be transfected into cells, e.g., yeast cells or eukaryotic cells, to provide for alternative glycosylation of proteins and lipids.

The instant invention is based, in part, on the discovery and cloning of a locus involved in the biosynthesis of gonococcal LOS has from gonococcal strain F62. The locus contains five open reading frames. The first and the second reading frames are homologous, but not identical to the fourth and the fifth reading frames respectively. Interposed is an additional reading frame which has distant homology to the *E. coli* rfaI and rfaJ genes, both glucosyl transferases involved in LPS core biosynthesis. The second and the fifth reading frames show strong homology to the lex-1 or lic2A gene of *Haemophilus influenzae*, but do not contain the CAAT repeats found in this gene. Deletions of each of these five genes, of combinations of genes, and of the entire locus were constructed and introduced into parental gonococcal strain F62 by transformation. The LOS phenotypes were then analyzed by SDS-PAGE and reactivity with monoclonal antibodies. Analysis of the gonococcal mutants indicates that four of these genes are the glycosyl transferases that add GalNAcβ1→3Galβ1→4GlcNAcβ1→3Galβ1→4 to the substrate Glcβ1→4Hep→R of the inner core region. The gene with homology to *E. coli* rfaI/rfaJ is involved with the addition of the α-linked galactose residue in the biosynthesis of the alternative LOS structure Galα1→4Galβ1→4Glcβ1→4Hep→R.

Since these genes encode LOS glycosyl transferases they have been named lgtA, lgtB, lgtC, lgtD and lgtE. The DNA sequence analysis revealed that lgtA, lgtC and lgtD contain poly-G tracts, which in strain F62 were respectively 17, 10 and 11 bp. Thus, three of the LOS biosynthetic enzymes are potentially susceptible to premature termination by reading-frame changes. It is likely that these structural features are responsible for the high frequency genetic variation of gonococcal LOS.

Abbreviations used throughout this specification include: Lipopolysaccharide, LPS; Lipooligosaccharide, LOS; N-Acetyl-neuraminic acid cytidine mono phosphate, CMP-NANA; wild type, wt; Gal, galactose; Glc, glucose; NAc, N-acetyl (e.g., GalNAc or GlcNAc).

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture"[R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A cell has been "transformed" by exogenous or heterologous DNA when such DNA has been introduced inside the cell; the cell may express a gene or genes encoded by such DNA. The transforming DNA may or may not be integrated (covalently linked) into chromosomal DNA making up the genome of the cell, or may be contained on an autonomous replicon. In prokaryotes, yeast, and mammalian cells for example, the transforming DNA may be maintained on an episomal element such as a plasmid. A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. Although the individual genes encoding glycosyltransferases of the invention are found in a single locus with very short non-coding sequences between them, phase variation resulting in deletion of any of lgtA, lgtB, or lgtC does not preclude reinitiation of transcription at the downstream genes. Thus, the locus provided herein includes transcription initiation sequences for transcription in Neisseria. Alternatively, the coding sequences of the invention can be engineered for expression under control of heterologous control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to translocate the polypeptide to the cell surface or to organelles within the cell, or secrete the polypeptide into the media, and this signal peptide is usually selectively cleaved by the protein transport machinery. Signal sequences can be found associated with a variety of proteins native to prokaryotes and eukaryotes. Incorporation of a signal sequence may be desirable for high level expression of a glycosyltransferase of the invention by bacteria, yeast, insect cells (baculovirus), or eukaryotic cells, to avoid affecting endogenous glycosyltransfer in the host cell.

A molecule is "antigenic" when it is capable of specifically interacting with an antigen recognition molecule of the immune system, such as an immunoglobulin (antibody) or T cell antigen receptor. As mentioned above, the carbohydrate (oligosaccharide) moiety of the LOS of Neisseria is an important antigenic determinant, which determines serotype of meningococcus (Zollinger and Mandrell, 1977, Infect. Immun. 18:424; Zollinger and Mandrell, 1980, Infect. Immun. 28:451). An antigenic portion of a molecule can be that portion that is immunodominant for antibody, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Pharmaceutically acceptable compositions of the invention are free of amounts of lipid A effective to cause a response in a mammalian subject, in particular a human subject.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et at., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Isolation of Genes for Genes for Glycosyltransferases

The present invention provides the full length coding sequence of the LOS locus of Neisseria, and thus, allows for obtaining any one or all five genes, termed herein lgt genes, encoding glycosyltransferases characteristic of that locus. Any Neisseria bacterial cell can potentially serve as the nucleic acid source for the molecular cloning of an lgt gene. In a specific embodiment, infra, the genes are isolated from *Neisseria gonorrhoeae*. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). For example, a *N. gonorrhoeae* genomic DNA can be digested with a restriction endonuclease or endonucleases, e.g. , Sau3A, into a phage vector digested with a restriction endonuclease or endonucleases, e.g., BamHI/EcoRI, for creation of a phage genomic library. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired lgt gene may be accomplished in a number of ways. For example, the generated DNA fragments may be screened by nucleic acid hybridization to the labeled probe synthesized with a sequence as disclosed herein (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for glycosyltransferases, e.g., SEQ ID NO:1.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, or functional properties, in particular glycosyltransferase activity the ability of a Lgt protein to mediate transfer of a sugar to an acceptor molecule. Alternatively, the putative let gene can be mutated, and its role as a glycosyltransferase established by detecting a variation in the structure of the oligosaccharide of LOS.

Alternatives to isolating the let genomic DNA include, but are not limited to, chemically synthesizing the gene sequence itself from a known sequence that encodes an Lgt, e.g., as shown in SEQ ID NO:1. In another embodiment, DNA for an let gene can be isolated PCR using oligonucleotide primers designed from the nucleotide sequences disclosed herein. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. In a specific aspect of the invention, the let coding sequence is inserted in an *E. coli* cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In specific embodiment, PCR primers containing such linker sites can be used to amplify the DNA for cloning. Recombinant molecules can be introduced into host cells via transformation, transfection, infection, electroporation, etc., so that many copies of the gene sequence are generated.

Transformation of host cells with recombinant DNA molecules that incorporate the isolated lgt gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding truncated forms of the enzyme (fragments) and derivatives of Lgt's that have the same functional activity as an Lgt. The production and use of fragments and derivatives related to an Lgt are within the scope of the present invention. In a specific embodiment, the fragment or derivative is functionally active, i.e., capable of mediating transfer of a sugar to an acceptor molecule.

Truncated fragments of the glycosyltransferases can be prepared by eliminating N-terminal, al, C-terminal, or internal regions of the protein that are not required for functional activity. Usually, such portions that are eliminated will include only a few, e.g., between 1 and 5, amino acid residues, but larger segments may be removed.

Chimeric molecules, e.g., fusion proteins, containing all or a functionally active portion of a glycosyltransferase of the invention joined to another protein are also envisioned. A glycosyltransferase fusion protein comprises at least a functionally active portion of a non-glycosyltransferase protein joined via a peptide bond to at least a functionally active portion of a glycosyltransferase polypeptide. The non-glycosyltransferase sequences can be amino- or carboxy-terminal to the glycosyltransferase sequences. Expression of a fusion protein can result in an enzymatically inactive glycosyltransferase fusion protein. A recombinant DNA molecule encoding such a fusion protein comprises a sequence encoding at least a functionally active portion of a non-glycosyltransferase protein joined in-frame to the glycosyltransferase coding sequence, and preferably encodes a cleavage site for a specific protease, e.g., thrombin or Factor Xa, preferably at the glycosyltransferase-non-glycosyltransferase juncture. In a specific embodiment, the fusion protein may be expressed in *Escherichia coli*.

In particular, Lgt derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an lgt gene may be used in the practice of the present invention. These include but are not limited to nucleotide sequences comprising all or portions of lgt genes that are altered by the substitution of different codons that encode the same amino acid residue within the sequence, thus producing a silent change. Likewise, the Lgt derivatives of the invention include, but are not limited to, those containing, as a primary amino acid sequence, all or part of the amino acid sequence of an Lgt including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding Lgt derivatives and analogs of the invention can be produced by various methods known in the art (e.g., Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Lgt, care should be taken to ensure that the modified gene remains within the same translational reading frame as the lgt gene, uninterrupted by translational stop signals, in the gene region where the desired activity is encoded.

Additionally, the lgt nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR *Technology: Principles and Applications for DNA Amplification*, H. Erlich, ed., Stockton Press, Chapter 6, pp. 61–70). It is notable in this regard that the lgtA, lgtB, and lgtC genes contain long poly-G stretches that are particularly susceptible to phase variation mutation.

Expression of a Glycosyltransferase

The gene coding for an Lgt, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native lgt gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Preferably, the periplasmic form of the Lgt (containing a signal sequence) is produced for export of the protein to the *Escherichia coli* periplasm or in an expression system based on *Bacillus subtillis*.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an glycosyltransferase or peptide fragment may be regulated by a second nucleic acid sequence so that the glycosyltransferase or peptide is expressed in a host transformed with the recombinant DNA molecule. For example, expression of an glycosyltransferase may be controlled by any promoter/enhancer element known in the art, but these regulatory elements must be functional in the host selected for expression. For expression in bacteria, bacterial promoters are required. Eukaryotic viral or eukaryotic promoters, including tissue specific promoters, are preferred when a vector containing an lgt gene is injected directly into a subject for transient expression, resulting in heterologous protection against bacterial infection, as described in detail below. Promoters which may be used to control lgt gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; and the like Expression vectors containing let gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted lgt gene. In the third approach, the recombinant vector/host system can be identified and selected based upon the presence or absence of certain "marker" gene functions (e.g.,β-galactosidase activity, PhoA activity, thymidine kinase activity, resistance to antibiotics, transformation phenotype, occlusion body formation in baculovirus, etc.) caused by the insertion of foreign genes in the vector. If the lgt gene is inserted within the marker gene sequence of the vector, recombinants containing the lgt insert can be identified by the absence of the marker gene function. In the fourth approach, recombinant expression vectors can be identified by assaying for the activity of the lgt gene product expressed by the recombinant. Such assays can be based, for example, on the physical or functional properties of the lgt gene product in in vitro assay systems, e.g., glycosyltransferase activity. Once a suitable host system and growth conditions are established, recombinant expression vectors can be propagated and prepared in quantity.

Biosynthesis of Oligosaccharides

The glycosyltransferases of the present invention can be used in the biosynthesis of oligosaccharides. The glycosyltransferases of the invention are capable of stereospecific conjugation of a specific activated saccharide unit to a specific acceptor molecule. Such activated saccharides generally consist of uridine, guanosine, and cytidine diphosphate derivatives of the saccharides, in which the nucleoside diphosphate serves as a leaving group. Thus, the activated saccharide may be a saccharide-UDP, a saccharide-GDP, or a saccharide-CDP. In specific embodiments, the activated saccharide is UDP-GlcNAC, UDP-GalNAc, or UDP-Gal.

The term "acceptor molecule" as used herein refers to the molecule to which the glycosyltransferase transfers an activated sugar. As is well known in the art, synthesis of carbohydrates proceeds by sequential coupling of sugar residues to a lipid, e.g., dolichol phosphate. In eukaryotic cells, which glycosylate proteins, the oligosaccharide or polysaccharide is transferred from the activated lipid carrier to the polypeptide on the luminal side of the endoplasmic reticulum. In prokaryotes, the carbohydrate can be synthesized directly on a lipid A molecule. It is likely that the glycosyltransferases of the invention may be sensitive to the core portion of the growing carbohydrate and the lipid molecule. Thus, in a preferred aspect, the acceptor molecule, or carrier, contains a lipid, preferably a polyisoprenoid alcohol lipid such as dolichol phosphate. Maximum synthetic efficiency may ensue from use of lipid A as the carrier. While the lipid A is not useful as a carrier for direct administration of the resulting oligosaccharide to a subject, e.g., as a vaccine preparation, it may be appropriate for use with a labile linkage for subsequent cleavage (under mild conditions) and separation of the oligosaccharide from the lipid carrier. It should further be noted that the glycosyltransferases will only work efficiently to add a specific activated saccharide to a saccharide residue on the acceptor molecule that corresponds to the natural acceptor molecule. For example, LgtE catalyzes transfer of Gal to Glcβ1→4Hep. Thus, where a glycosyltransferase mediates attachment of GalNAc to Glc, the nature of the Glc residue (whether it is attached directly or indirectly to the carrier, for example) will affect the reaction efficiency. It is unlikely that efficient synthesis can occur in the absence of a carrier, or using other than a lipid carrier. However, even inefficient synthesis may be desirable, and practice of the present invention is not limited to use of acceptor molecules containing lipids, but extends to saccharides, polysaccharides, polypeptides, glycoproteins, and the like.

For the synthesis of an oligosaccharide, a glycosyltransferase is contacted with an appropriate activated saccharide and an appropriate acceptor molecule under conditions effective to transfer and covalently bond the saccharide to the acceptor molecule. Conditions of time, temperature, and pH appropriate and optimal for a particular saccharide unit transfer can be determined through routine testing; generally, physiological conditions will be acceptable. Certain co-reagents may also be desirable; for example, it may be more effective to contact the glycosyltransferase with the activated saccharide and the acceptor molecule in the presence of a divalent cation.

According to the invention, the glycosyltransferase enzymes can be covalently or non-covalently immobilized on a solid phase support such as SEPHADEX, SEPHAROSE, or poly(acrylamide-co-N-acryloxysucciimide) (PAN) resin. A specific reaction can be performed in an isolated reaction solution, with facile separation of the solid phase enzyme from the reaction products. Immobilization of the enzyme also allows for a continuous biosynthetic stream, with the specific glycosyltransferases attached to a solid support, with the supports arranged randomly or in distinct zones in the specified order in a column, with passage of the reaction solution through the column and elution of the desired oligosaccharide at the end. An efficient method for attaching the glycosyltransferase to a solid support and using such immobilized glycosyltransferases is described in U.S. Pat. No. 5,180,674, issued Jan. 19, 1993 to Roth, which is specifically incorporated herein by reference in its entirety.

An oligosaccharide, e.g., a disaccharide, prepared using a glycosyltransferase of the present invention can serve as an acceptor molecule for further synthesis, either using other glycosyltransferases of the invention, or glycosyltransferases known in the art (see, e.g., Roth, U.S. Pat. No. 5,180,674, and Roth, International Patent Publication No. WO 93/13198, published 8 Jul. 1993, each of which is incorporated herein by reference in its entirety). The oligosaccharide compositions of the invention are useful in a wide variety of therapeutic and diagnostic applications. For example, the saccharide compositions can be used as blocking agents for cell surface receptors in the treatment of numerous diseases involving cellular adhesion. Alternatively, saccharide compositions useful as nutritional supplements, antibacterials, anti-metastases agents, anti-inflammatory agents (e.g., for binding to inflammatory-associated lectins or cell surface receptors), to mention but a few, are contemplated by the instant invention. As noted above, the glycosyltransferases of the invention can be used in conjunction with other glycosyltransferases known in the art or to be discovered to synthesize complex oligosaccharides or polysaccharides.

Alternatively, the glycosyltransferases of the invention can be used to synthesize oligosaccharides representative of the oligosaccharides found on various strains of Neisseria. For example, by deleting open reading frames from the locus, or by selecting only a few of the glycosyltransferases of the invention for synthesis, alternative oligosaccharide structures can be prepared. These can be used in vaccine preparations effective against Neisseria variants, in particular, subunit vaccines against gonococcus and meningococcus.

Alternatively, the glycosyltransferases of the present invention can be used to prepare oligosaccharides corresponding to oligosaccharides associated with human glycolipids. Thus, in specific embodiments, the present invention provides for synthesis of an oligosaccharide corresponding to lacto-N-neotetraose of the sphingolipid paragloboside; an oligosaccharide that mimics gangliosides; and a mimic of the saccharide portion of globoglycolipids, which is the structure characteristically found in *Neisseria meningitidis* immunotype L1. The oligosaccharides of the present invention correspond to the core oligosaccharides of the blood group antigens, and therefore have great utility in the preparation of such blood group antigens for diagnostic or therapeutic purposes.

Accordingly, a method for preparing an oligosaccharide having the structure GalNAcβ1→3Galβ1→4GlcNAcβ1→3Galβ1→4Glc (i.e., ganglioside) comprises sequentially performing the steps of:

a. contacting a reaction mixture comprising an activated Gal to an acceptor moiety comprising a Glc residue in the presence of a glycosyltransferase having an amino acid sequence of SEQ ID NO:6, or a functionally active fragment thereof;

b. contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11, or a functionally active fragment thereof;

c. contacting a reaction mixture comprising an activated Gal to the acceptor moiety comprising a GlcNAcβ1→3Galβ1→4Glc residue in the presence of a glycosyltransferase having an amino acid of SEQ ID NO:8; and d. contacting a reaction mixture comprising an activated GalNAc to the acceptor moiety comprising a Galβ1→4GlcNAcβ1→3Galβ1→4Glc residue in the presence of a glycosyltransferase having an amino acid sequence of SEQ ID NO:5 or SEQ ID NO:12, or a functionally active fragment thereof.

Similarly, a method for preparing an oligosaccharide having the structure Galβ1→4GlcNAcβ1→3Galβ1→4Glc (i.e., lacto-N-neotetraose) comprises sequentially performing the steps of:

a. contacting a reaction mixture comprising an activated Gal to an acceptor moiety comprising a Glc residue in the presence of a glycosyltransferase having an amino acid sequence of SEQ ID NO:6, or a functionally active fragment thereof;

b. contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11, or a functionally active fragment thereof; and c. contacting a reaction mixture comprising an activated Gal to the acceptor moiety comprising a GlcNAcβ1→3Galβ1→4Glc residue in the presence of a glycosyltransferase having an amino acid of SEQ ID NO:8.

In another embodiment, a method for preparing an oligosaccharide having the structure Galα1→4Galβ1→4Glc (i.e., globoglycolipids) comprises sequentially performing the steps of:

a. contacting a reaction mixture comprising an activated Gal to an acceptor moiety comprising a Glc residue in the presence of a glycosyltransferase having an amino acid sequence of SEQ ID NO:6, or a functionally active fragment thereof; and b. contacting a reaction mixture comprising an activated Gal to the acceptor moiety comprising Galβ1→4Glc in the presence of a glycosyltransferase having an amino acid sequence of SEQ ID NO:4, or a functionally active fragment thereof.

Such oligosaccharides can be prepared using lipid A as a carrier. Preferably, if the resulting glycolipid is to be used in a vaccine, a non-toxic lipid, such as dolichol phosphate, is used as the carrier.

Vaccination

Active immunity against Neisseria strains can be induced by immunization (vaccination) with an immunogenic amount of an oligosaccharide prepared according to the present invention in admixture with an adjuvant, wherein the oligosaccharide is the antigenic component of the vaccine. Preferably, the oligosaccharide is conjugated to a carrier protein. Alternatively, where the antigen is a glycolipid, it can be incorporated in a liposome.

The oligosaccharide alone cannot cause bacterial infection, although the oligosaccharide on lipid A is toxic, and the active immunity elicited by vaccination according to the present invention can result in immediate immune response.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

A vaccine of the invention, i.e., a vaccine comprising an oligosaccharide corresponding to an antigenic determinant on a strain of Neisseria, can be administered via any parenteral route, including but not limited to intramuscular, intraperitoneal, intravenous, and the like.

Administration of an amount of a Neisseria oligosaccharide sufficient to inhibit adhesion of the bacterium to its target cell may also be effective for treating meningococcal or gonococcal infection. The required amount can be determined by one of ordinary skill using standard techniques.

Expression of Glycosyltransferases in for Intracellular Glycosylation

The present invention further contemplates transforming a host cell with a glycosyltransferase or glycosyltransferases of the invention. It is expected that expression of the glycosyltransferase, possibly in a cell lacking one or more endogenous glycosyltransferases, may result in novel glycosylation of lipids and proteins in such eukaryotic cells, and novel glycosylation of lipids in procaryotic cells.

For example, transformation of a bacterium with non-toxic lipid molecules may provide for expression of Neisseria oligosaccharides on such a bacterium, which can then be used directly in a whole cell vaccine.

Alternatively, expression of such a glycosyl transferase in yeast, insect, or mammalian cell lines may result in novel glycosylation of lipids and proteins expressed by these cells.

Antibodies to Neisseria Oligosaccharides, and Diagnosis and Therapy Therewith Just as the oligosaccharides can be used in vaccines, so too they can be used to generate antibodies to themselves, which antibodies, in turn, can be used to detect that particular strain of bacteria or for passive immunity. Antibodies include but are not limited to polyclonal, monoclonal, chimeric, single chain, Fab fragments, and an Fab expression library. Various procedures known in the art may be used for the production of polyclonal antibodies to oligosaccharide. For the production of antibody, various host animals can be immunized by injection with the oligosaccharide, including but not limited to rabbits, mice, rats, sheep, goats, etc. In one embodiment, the oligosaccharide can be conjugated to an immunogenic carrier, e.g., bovine serum albumin (BSA) or keyhole limpet hemocyanin (KLH). Various adjuvants may be used to increase the immunological response, depending on the host species. For preparation of monoclonal antibodies directed toward the oligosaccharide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an oligosaccharide together with genes from a human antibody molecule of appropriate biological activity can be used; such antibodies are within the scope of this invention. Such human or humanized chimeric antibodies are preferred for use in therapy of human diseases or disorders, since the human or humanized antibodies are much less likely than xenogenic antibodies to induce an immune response, in particular an allergic response, themselves. According to the invention, techniques described for the production of single chain antibodies (U.S. Pat. No. 4,946,778) can be adapted to produce oligosaccharide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an oligosaccharide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific oligosaccharide, one may assay generated hybridomas for a product which binds to an oligosaccharide containing such epitope. For selection of an antibody specific to an oligosaccharide from a particular species or strain of Neisseria, one can select on the basis of positive binding with oligosaccharide expressed by or isolated from cells of that species or strain.

The foregoing antibodies can be used in methods known in the art relating to the localization and activity of the oligosaccharide, e.g., for Western blotting, imaging oligosaccharide in situ, measuring levels thereof in appropriate physiological samples, etc.

Diagnosis of infection with a Gram positive bacterium can use any immunoassay format known in the art, as desired. The antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

Alternatively, the nucleic acids and sequences thereof of the invention can be used in the diagnosis of infection with Neisseria, in particular, to identify a particular strain, or to determine which, if any, of the glycosyltransferase genes are mutated. For example, the lgt genes or hybridizable fragments thereof can be used for in situ hybridization with a sample from a subject suspected of harboring an infection of Neisseria bacteria. In another embodiment, specific gene segments of a Neisseria can be identified using PCR amplification with probes based on the lgt genes of the invention. In one aspect of the invention, the hybridization with a probe or with the PCR primers can be performed under stringent conditions, or with a sequence specific for a unique strain or a limited number of strains of the bacterium, or both, thus allowing for diagnosis of infection with that particular strain (or strains). Alternatively, the hybridization can be under less stringent conditions, or the sequence may be homologous in any or all strains of a bacterium, thus allowing for diagnosis of infection with that species.

The present invention will be better understood from a review of the following illustrative description presenting the details of the constructs and procedures that were followed in its development and validation.

EXAMPLE

This Example describes a locus in *Neisseria gonorrhoeae* strain F62 containing five genes. Four of the genes are responsible for the sequential addition of the GalNAcβ1→3Galβ1→4GlcNAcβ1→3Galβ1→4 to the substrate Glcβ1→4Hep→R of the inner core region (Yamasaki et al., 1991, Biochemistry 30:10566). The fifth gene is involved with the addition of the α-linked galactose residue in the biosynthesis of the alternative LOS structure Galα1→4Galβ1→4Glcβ1→4Hep→R (John et al., 1991, J. Biol. Chem. 266:19303). The DNA sequence analysis revealed that the first, third and fourth reading frames contained poly-G tracts which in strain F62 were respectively 17, 10 and 11 bp. Thus, three of the LOS biosynthetic enzymes are potentially susceptible to premature termination by reading-frame changes, as has been reported for the gonococcal pilC genes (Jonsson et al., 1991, EMBO J. 10:477; Rudel et al., 1992, Molec. Microbiol. 6:3439). It is likely that these structural features are responsible for the high-frequency genetic variation of gonococcal LOS (Schneider et al., 1988, Infect. Immun. 56:942).

Materials and Methods

Reagents and chemicals. Most laboratory chemicals were obtained from Sigma Chemical Co (St. Louis, Mo.). Restriction enzymes were purchased from New England Biolabs (Beverly, Mass.).

Media and growth conditions. *E. coli* strains were grown in solid or liquid LB medium (Sambrook et al., 1989, Cold Spring Harbor Laboratory Press, Cold Spring Harbor); antibiotics were added as applicable. Carbenicillin was used at 50 µg/ml and erythromycin at 200 µg/ml. *Neisseria gonorrhoeae* strain F62 was grown on GC agar (Swanson, 1978, Infect. Immun. 19:320) or GC agar containing 2 µg/ml erythromycin. For isolation of LOS or genomic DNA, gonococci were grown in 1.5% proteose peptone broth (Difco Laboratories, Detroit Mich.), 30 mM phosphate, 8.5 mM NaCl supplemented with 1% isovitalex (Becton Dickinson Microbiology Systems, Cockeysville, Md.).

Recombinant DNA methods. Plasmids were purified using either Qiagen columns or the QIAprep spin columns obtained from Qiagen Inc. (Chatsworth, Calif.). Digestion with restriction enzymes, gel electrophoresis, ligations with T4 DNA polymerase and transformation of *E. coli* were done according to Sambrook et al. (Sambrook et al., 1989, Cold Spring Harbor Laboratory Press, Cold Spring Harbor). Southern hybridization was performed on Hybond N+ membranes Amersham Co. (Arlington Heights, Ill.) with DNA labeled using the ECL kit from Amersham Co. Genomic DNA was isolated as described by Moxon et al. (Moxon et al., 1984, J. Clin. Invest. 73:298).

A gene bank of *Neisseria gonorrhoeae* strain F62 genomic DNA was constructed by ligating ca 20 kb fragments obtained by incomplete digestion with Sau3A into BamHI/EcoRI digested λ2001 (Karn et al., 1984, Gene 32:217). The phage library was screened by hybridization with random primer-labeled plasmid pR10PI, and 5 clones were isolated by plaque purification. The phage from these clones were purified by sedimentation followed by flotation on CsCl (Davis et al., 1980, Cold Spring Harbor Laboratory, Cold Spring Harbor, N.Y.), and the DNA was isolated. From one of these clones, two ClaI fragments of 4.9 and 3.4 kb were isolated by gel electrophoresis and recovery with Geneclean II (BIO 101 Inc., La Jolla, Calif.). These were ligated into ClaI cut pBluescript II SK- from Stratagene (La Jolla, Calif.) and called p4900 and p3400 respectively. p4900 contained a PstI site in the insert and was subdivided into two clones containing inserts of 2.1 and 2.8 kb. The clone containing the 2.8 kb insert was called pPstCla. The inserts in p3400 and pPstCla were sequenced by the chain termination method (Sanger et al., 1977, Proc. Natl. Acad Sci. USA 74:5463) using Sequenase II, (United States Biochemical Co., Cleveland. Ohio). All of the sequence presented in SEQ ID NO:1 was completed in both directions.

Figure 6:
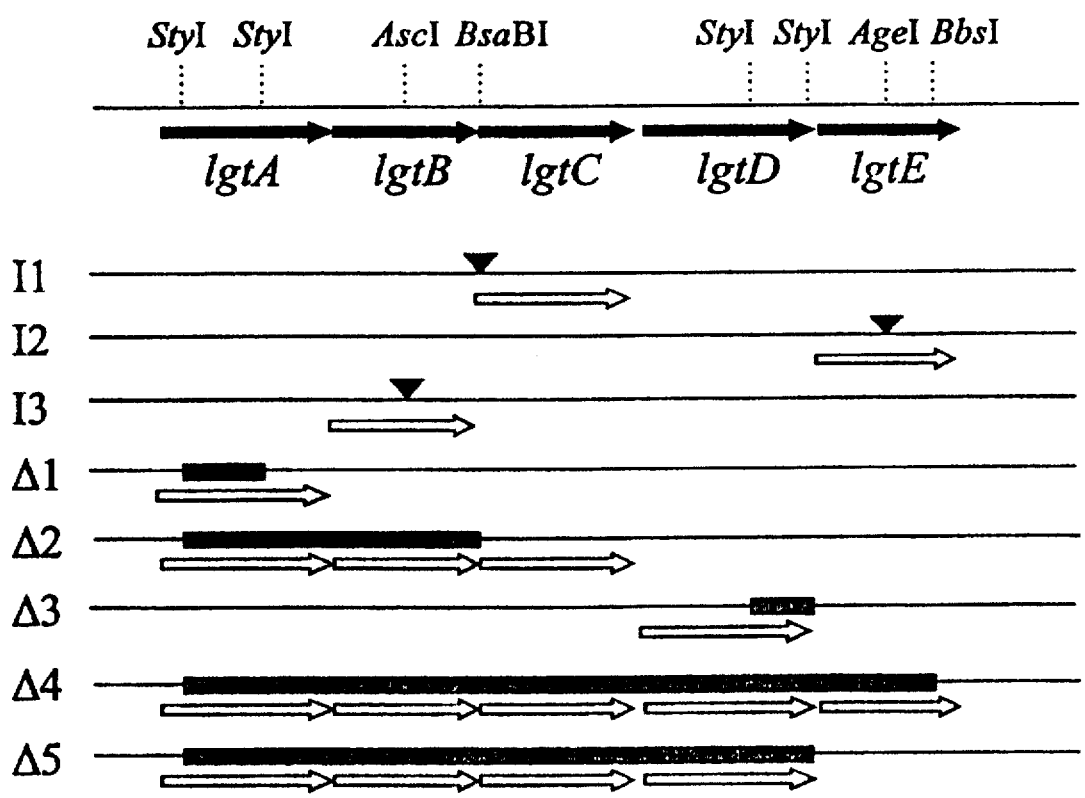
FIG. 6: Deletions in the LOS locus. Three insertion and five deletions of the LOS locus were constructed as detailed in the methods section. The restriction sites that were used are indicated. The insertions are marked by triangles and the extent of the deletions by stippled boxes. The open arrows indicate the open reading frames disrupted by the construction. In each of the constructs the erythromycin marker ermC' was inserted at the site of the insertion or the deletion.

The insertion and deletions shown in FIG. 6 were constructed as follows. I1, I3, Δ1 and Δ2 used plasmid pPstCla cut respectively with BsaBI, AscI, StyI and double cut with StyI and BsaBI. I2 and Δ3 used plasmid p3400 cut with AgeI or StyI. The complete locus was assembled by cloning the ClaI-ApaI fragment from p3400 into pPstCla cut with ClaI and ApaI, and the plasmid was called pLOS5. Deletions Δ4 and Δ5 were constructed using pLOS5 and digestion with StyI and BbsI or with StyI alone. In all instances (except digestion with BsaBI) the cut plasmids were treated with the Klenow fragment of *E. coli* DNA polymerase to blunt the ends, and ermC' (erythromycin resistance marker) was inserted. The ermC' gene was isolated from plasmid pIM13 (Projan et al., 1987, J. Bacteriol. 169:5131) as a ClaI-HindIII fragment and cloned into the same sites in plasmid pHSS6 (Seifert et al., 1986, Proc. Natl. Acad. Sci. USA 83:735). From this plasmid it was excised as a NotI fragment, the ends blunted by treatment with Klenow fragment of DNA polymerase, purified by gel electrophoresis and recovery with Geneclean II.

Transformation of piliated *Neisseria gonorrhoeae* strain F62 was performed with plasmids isolated from *E. coli* (Klugman et al., 1989, Infect. Immun. 57:2066) and the transformants selected on GC agar (Swanson, 1978, Infect. Immun. 19:320) containing 2 µg/ml erythromycin. The fidelity of the genomic alteration of each of the gonococcal transformants was verified by sequencing the upstream and downstream junctions of the ermC' gene in their genomic DNA using a PCR technique. Two 5' biotinylated primers, GCCGAGAAAACTATTGGTGGA (SEQ. ID. NO:9) and AAAACATGCAGGAATTGACGAT) (SEQ. ID. NO:10), were synthesized; these were based on the ermC' sequence near its upstream and its downstream end respectively. The primers were designed such that their 3' ends pointed outward from the ermC' gene. Each of these primers was used together with a suitable primer matching the sequence of the LOS locus near the putative insertion. PCR was performed according the instructions supplied with the GeneAmp PCR Reagent Kit from Perkin Elmer (Branchburg, N.J.) using 25 cycles. In all instances the expected size product was obtained. The DNA sequence of these products was determined by purifying the PCR product on magnetic streptavidin beads from Dynal, Inc. (Lake Success, N.Y.) and sequencing with the Sequenase II kit according to a protocol provided by Dynal, Inc., based on the method developed by Hultman et al (Hultman et al., 1989, Nucleic Acids Res. 17:4937). The sequences were analyzed by computer programs in the GCG package of Genetics Computer Group, Inc. (Madison, Wis.).

Immunological methods. Monoclonal antibodies 17-1-L1 (L1), 9-2-L378 (L3), 2-1-L8 (L8) were obtained as filtered ascites fluids. Antibody 1-1-M was obtained as ascites fluid and 3F11 and 4C4 were obtained as tissue culture supernatants. LOS was extracted from each of the gonococcal mutants by the hot phenol-water method (Westphal and Jann, 1965, Academic Press, New York.83–91) and purified as described (Johnston et al., 1976, J. Exp. Med. 143:741). The LOS was diluted to 200 µg/ml in the Western blot buffer described by Towbin et al. (Towbin et al., 1979, Proc. Natl. Acad. Sci. USA 76:4350), and 1.5 µl aliquots were spotted on Immobilon-P membrane from Millipore Corp (Bedford, Mass.) that was lying on 3MM Whatman filter paper (Whatman Ltd., Maidstone, England) soaked in the blotting buffer. The spots were allowed to absorb into the membrane over a period of 2 min and the strips were placed in blocking buffer for at least 60 min. The blocking buffer consisted of 3% gelatin dissolved in 150 mM NaCl, 10 mM Tris-HCl 10 mM pH 7.5, 5 mM MgCl$_2$, 0.02% NaN$_3$. The strips were washed thrice in the same buffer containing 1% gelatin. The strips were treated for 2 h with monoclonal antibodies diluted in blocking buffer. The antibodies available as ascites fluids were diluted 1/1000, antibodies available as tissue culture supernatants 1/10. The strips were washed, incubated for 60 min with a 1/1000 dilution of phosphatase-conjugated anti-IgG,IgA,IgM from Cappel (Organon Teknika Co., West Chester, Pa.), washed and stained as described previously (Blake et al., 1984, Analyt. Biochem. 136:175).

Gel electrophoresis. Gel electrophoresis of LOS samples was performed as described by Lesse et al (Less et al., 1990, J. Immunol. Meth. 126:109) and the gels silver stained (Hitchcock and Brown, 1983, J. Bacteriol. 154–269).

Results

Cloning of the LOS Locus. During attempts to isolate the porin gene of *Neisseria gonorrhoeae*, pBR322 clones containing a 4.9 kb ClaI fragment that reacted by colony blots with a rabbit antiserum to purified porin were repeatedly isolated. An immunoreactive subclone, pR10PI, consisting of a 1305 bp RsaI-ClaI fragment was derived and its DNA sequence was determined. This sequence had homology to a gene isolated from *Haemophilus influenzae* called lex-1 (Cope et al., 1991, Molec. Microbiol. 5:1113) or lic2A (High et al., 1993, Molec. Microbiol. 9:1275) that is known to be involved in LPS synthesis of that species. Using subclone pR10PI as a probe, Southern blots of *Neisseria gonorrhoeae* genomic DNA digested with ClaI revealed hybridization with two fragments, 4.9 and 3.4 kb. However, digestion with some other restriction enzymes gave rise to only a single band. Notably, digestion with BfaI gave rise to a single band of 4.1 kb, suggesting that the two copies were closely linked (data not shown).

A λ2001 bank of *Neisseria gonorrhoeae* strain F62 DNA was screened by hybridization with pR10PI and 5 clones were isolated. One of these clones, when digested with either ClaI or BfaI and examined by Southern hybridization using pR10PI as the probe, gave rise to a pattern identical to that seen with genomic DNA. The appropriate ClaI fragments of this λ2001 clone were isolated and cloned into the ClaI site of pBluescript II SK-. The entire sequence of the 3400 ClaI fragment was determined. Mapping of the clone containing the 4900 bp ClaI fragment indicated that there was a single PstI site in the clone about 2.8 kb from one side, allowing the clone to be divided into two subclones. Partial sequence of the ends of the 2.1 kb subclone indicated that it contained a coding frame homologous to the *E. coli* COOH-terminal portion of the α subunit of glycyl-tRNA synthetase (glyS) and the majority of the µ subunit of this gene (Webster et al., 1983, J. Biol. Chem. 258:10637). The predicted length of DNA needed to match the *E. coli* sequence was present; this clone was not examined further.

DNA Sequence of the LOS Locus. A summary of the features found by sequencing the two clones is illustrated in FIG. 2. Following the glyS gene were found five closely spaced open reading frames. The last frame has 46 bp downstream of the termination codon a sequence typical of a rho independent termination signal. Subsequently, there is an area of ca 100 bp that has striking homology to the IS1106 neisserial insertion sequence (Knight et al., 1992, Molec. Microbiol. 6:1565). Further elucidation of the nature of this locus, presented below, showed the five open reading frames code for LOS glycosyl transferases and hence they have been named lgtA - lgtE.

Searches for internal homology within this locus indicates that the DNA coding for the first two genes (lgtA, lgtB) is repeated as the fourth and fifth genes (lgtD, lgtE) and that interposed is an additional open reading frame, lgtC. This is in keeping with the data obtained by Southern hybridization presented above, in which pR10PI probe containing the lgtB and a small portion of the lgtC gene hybridized with two ClaI fragments, but with only one BfaI fragment (see positions of the BfaI sites in the LOS locus in FIG. 2). In more detail, 16 bp following the stop codon of the tRNA synthetase (glyS) is the beginning of a stem loop structure followed closely by a consensus ribosome binding site (rbs), and within 6 bp is a TTG believed to be the initiation codon of lgtA. 2871 bp downstream from the beginning of the stem loop (closely following the stop codon of lgtC) there is an almost perfect repeat of the stem loop structure, the rds and the TTG initiation codon of lgtD, with the downstream sequence strongly homologous for about 500 bp. The sequences then diverge to some extent. However, at the beginning of lgtB and lgtE the homology again becomes nearly perfect for ca 200 bases to then diverge toward the latter part of the orfs. The similarity of the homologous proteins is illustrated in FIGS. 3 and 4. These comparisons, demonstrate the near-perfect conservation of the primary structure in the N-terminal portions of the molecules with increasing divergence toward the COOH-termini of the proteins.

The lgtC sequence interposed between the repeated portions of the locus is not repeated within the locus or in the

*Neisseria gonorrhoeae* genome (data not shown). It appears to be homologous to *E. coli* rfaI or rfaJ genes, which are very closely related genes that serve as glucosyl transferases in core LPS biosynthesis (Pradel et al., 1992, J. Bacteriol. 174:4736). The similarity of rfaI with lgtC is illustrated in FIG. 5.

It was found that three of these genes contained within their coding frame runs of guanosines coding for stretches of glycines (see FIG. 2). These poly-G regions were found in lgtA (17 bp), lgtC (10 bp) and lgtD (11 bp); in each case the number G residues was one that maintained an intact reading frame (see FIGS. 3 and 5). In each of the three genes a change of 1 or 2 G bases would cause premature termination of the transcript.

LOS phenotype of *Neisseria gonorrhoea* F62 with deletions of the LOS locus. In order to define the function of the lgt genes, insertions or deletions of the LOS locus were constructed in plasmids propagated in *E. coli*. The insertions or deletions in each case were marked with the ermC" gene, which is an excellent selective marker in *Neisseria gonorrhoeae* (Klugman et al., 1989, Infect. Immun. 57:2066). The constructions are summarized in FIG. 6. I1, I2 and I3 refer to insertions of the ermC" marker into, respectively, a BsaBI, AgeI and AscI site. Similarly, the deletions were constructed by excising portions of the plasmids and substituting the erythromycin marker. The open arrows indicate the gene or genes disrupted. Each of these plasmids was used to transform *Neisseria gonorrhoeae* strain F62 and transformants were selected on erythromycin-containing plates. The fidelity of the genomic alteration of a prototype of each of the gonococcal transformants was verified by sequencing the upstream and downstream junction of the ermC" gene. To simplify the nomenclature in this report the gonococcal mutants have been given the same names used to identify the plasmid constructs in FIG. 6.

Figure 7:
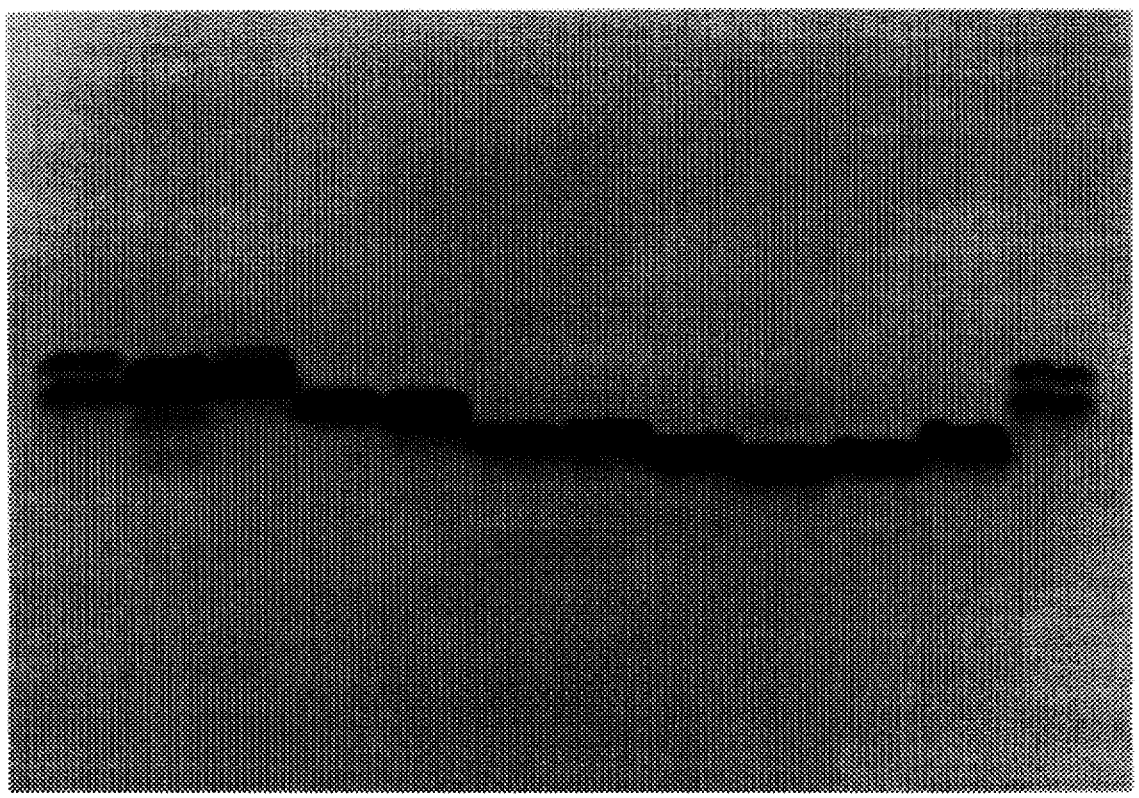
FIG. 7: Silver-stained SDS-PAGE of LOS preparations. Gel electrophoresis of purified LOS samples of 375 ng was performed and stained as described in materials and methods. Above the gel are indicated the structure of the LOS of the major bands inferred to be present in each of the preparations. These structures are based on the reactivity with monoclonal antibodies shown in FIG. 8, but are presented in this Figure to facilitate interpretation of the patterns observed. R stands for the inner core region and lipid A. 1291e is a pyocin resistant mutant (Dudas and Apicella, 1988, Infect. Immun. 56:499)

The LOS of the mutants were examined by SDS-PAGE and compared to the LOS of strain 1291e. This strain was originally isolated by Dudas and Apicella (Dudas and Apicella, 1988, Infect. Immun. 56:499) as a pyocin-resistant mutant of strain 1291 wild type and has been extensively characterized both chemically and genetically. Chemical analysis has shown that this mutant lacks completely the lacto-N-neotetraose substitution on heptose 1 (John et al., 1991, J. Biol. Chem. 266:19303). The genetic basis of this mutant has been defined (Zhou et al., 1994, J. Biol. Chem. 269:11162; Sandlin and Stein, 1994, J. Bacteriol. 176:2930); it is a mutation of the pgm gene coding for phosphoglucomutase. This mutation prohibits the synthesis of UDP-glucose and hence the addition of glucose to the heptose. As seen in FIG. 7, the parental wild type F62 strain gives rise to two major LOS bands; their appearance is indistinguishable from SDS-PAGE patterns previously published by other workers (Schneider et al., 1985, Amer. Soc. Microbiology, Washington 400–405). The mutants are arranged on the gel according to the size of the major band that they contain. The size decreases from the top band of the F62 wt LOS in four clear steps to the size of the LOS of Δ4 or I2. Since the I2 mutant (with an insertion into lgtE, the last gene in the locus) has the same phenotype as Δ4 (which has a complete deletion of the locus), it suggests that the lgtE product performs the first biosynthetic step. Thus, the enzymes encoded by lgtA-D, although intact, do not have a substrate to act upon. Mutant Δ5 (a deletion of the locus with the exception of lgtE) gives rise to a LOS that is one step larger, supporting the idea that this gene accounts for the initial biosynthetic step. Note that the LOS of both I2 and Δ4 mutants is perceptibly larger than the LOS of strain 1291e which is known to be unable to add glucose, the first residue in the lacto-N-neotetraose chain. These data suggest that lgtE encodes the galactosyl transferase enzyme which adds the first galactose of the lacto-N -neotetraose.

Figure 8:
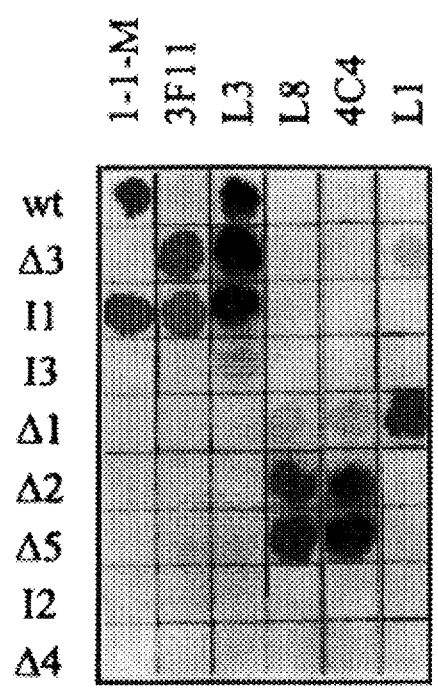
FIG. 8: Reactivity of LOS from strain F62 wt and mutants with monoclonal antibodies. The names of the following monoclonal antibodies were abbreviated: 17-1-L1 (L1), 9-2-L378 (L3), 2-1-L8 (L8). Purified LOS was applied Immobilon-P membranes, allowed to react with the antibodies and developed as described in materials and methods. The specificity of the monoclonal antibodies is summarized in FIG. 1.

The LOS preparations were also studied using a dot blot technique for their reactivity with monoclonal antibodies. The monoclonal antibodies employed and their reported specificities are shown in FIG. 1. The reactions observed with the LOS obtained from the parental strain and the mutants are summarized in FIG. 8. The reactivity of the parental F62 with 1-1-M, 3F11 and L8 was as reported previously by Mandrell et al (Mandrell et al., 1985, Amer. Soc. Microbiology, Washington 379–384) and by Yamasaki et al (Yamasaki et al., 1991, Mol. Immunol. 28:1233). Mutants Δ4 and I2 fail to react with any of the antibodies. However, Δ5 gives a strong reaction with antibodies 4C4 and L8, indicating that the first galactose residue is present. This is in keeping with the SDS-PAGE results (see FIG. 6) and supports the role of lgtE as the galactosyl transferase. It also indicates that deletions upstream of lgtE do not significantly inactivate its function by polar effects. The LOS of F62 wt parent has strong reactivity with L3 and weak reactivity with 3F11. It is known that reactivity 3F11 is occluded by the addition of the GalNAc residue (Schneider et al., J. Exp. Med. 174:1601); this is not the case with the L3 antibody. The wt LOS reacts with 1-1-M, the antibody reactive when the terminal GalNAc residue is present. The reactivity with 1-1-M is lost in Δ3 which has a deletion only in lgtD. This suggest that this gene encodes the GalNAc transferase.

The reactivity with antibody L1 (specific for the alternative LOS structure capped with an α1→4Gal) is not seen in wt LOS, is absent in I1, and all deletions which affect lgtC. The reactivity is strongest in Δ1, which has a deletion of lgtA only. Note that this mutant also has lost reactivity with 3F11 and L3. These two findings suggest that lgtA codes for the GlcNAc transferase, and when this residue is not added, the incomplete chain is a substrate for the action of lgtC to produce the alternative LOS structure. Note that the sizes of the LOS products seen in FIG. 7 are in accord with the immunological data. This conclusion suggests that lgtC encodes the α-Gal transferase. This is further supported by the weak reactivity of mutant Δ3 with antibody L1. Mutant Δ3 has a deletion of lgtD and fails to add the terminal GalNAc, allowing the α-Gal transferase to modify the lacto-N-neotetraose group to produce a $P_k$-like globoside (Mandrell, 1992, Infect. Immun. 60:3017). Mutant I3 (with inactive lgtB) has lost reactivity with 1-1-M, 3F11 and L1, and remains only weakly reactive with L3. Together with the size of the product, these observations suggest that lgtB encodes the galactosyl transferase adding Galβ1→4 to the GlcNAc residue. Ricinus lectin RCA-I is specific for terminal galactose in β linkage (Nicolson and Blaustein, 1972, Biochim. Biophys. Acta 266:543; Lin and Li, 1980, Eur. J. Biochem. 105:453) and was used to confirm the presence of this structure on the LOS preparations. Using ELISA tests it was found that wild type, Δ3, Δ2 and Δ5 LOS, expected to bear a terminal βGal, bound the lectin (see FIG. 7), while Δ4, I2, Δ1 and I3 were unreactive (data not shown).

Discussion

A locus containing 5 open reading frames has been cloned. The effect of eight defined mutations within this locus on the size and serological reactivity of the LOS produced by gonococcal transformants suggests that these genes are the glycosyl transferases responsible for the biosynthesis of most of the lacto-N-neotetraose chain. The data obtained allow an identification of the function of each of these genes. It is noteworthy that lgtB and lgtE, which are structurally very closely related, also perform an apparently very similar biosynthetic task, i.e. the addition of Galβ1→4 to GlcNAc or Glc, respectively. Similarly, the closely related lgtA and lgtD add GalNAc or GlcNAc β1→3, respectively, to a Gal residue. lgtC, which is unrelated to the other genes in the locus, is responsible for the addition of a Galα1→4.

The DNA sequence showed that three of the genes (lgtA, lgtC and lgtD) contain tracts of guanosines which code for glycine residues in the proteins. These provide a potential mechanism for high-frequency variation of expression of these genes. Slippage in such poly-G tracts is well documented to control the expression of the gonococcal pilC genes, with resultant effects on pilus adhesiveness to human epithelial cells (Rudel et al., 1992, Molec. Microbiol. 6:3439). In strain F62, the numbers of bases in each of the three poly-G regions were such that the proteins are in frame, and this is in keeping with the ability of F62 wild type to produce a complete LOS including the addition of the terminal GalNAc.

Three aspects of LOS biosynthesis appear potentially to be subject to high frequency variation. The first is the addition of the terminal GalNAc (lgtD). This would cause an alteration of reactivity with monoclonal antibody 1-1-M, and this phase variation has been reported by van Putten (Van Putten, 1993, EMBO J. 12:4043). Similarly, a change in lgtA would cause the failure of the addition of GlcNAc to the growing chain and truncate the LOS at the β-lactosyl level. This is a very common form of LOS in gonococci with a 3.6 kilodalton molecule, which confers resistance to the bactericidal effect of normal human serum (Schneider et al., 1985, Infect. Immun. 50:672). It is tempting to speculate that the in vitro variation between variant A and C of MS11$_{mk}$ from the β-lactosyl chain to a complete LOS (which had a selective advantage in vivo in the volunteers) could be explained by regaining functional expression, of the GlcNAc transferase lgtA. Finally, the variable addition of α1→4Gal to either the β-lactosyl ($p^k$-like globotriose) or the lacto-N-neotetraose group ($P_j$-like globoside) (Mandrell, 1992, Infect. Immun. 60:3017) would be under the control of the expression of lgtC. The activity of the lgtC transferase appears to compete poorly with the other transferases for precursor and its activity is evident only if either lgtA or lgtD are silent. For the Galα1→4Galβ1→4Glc trisaccharide to be synthesized the GlcNAc transferase lgtA must be inactive and for expression of the $P_j$-like globoside Galα1→4Galβ1→4GlcNAcβ1→3Galβ1→4Glc the GalNAc transferase lgtD must be silent.

Comparable high frequency antigenic variation of *Haemophilus influenzae* LOS has also been noted and has been attributed to changes in translational frame caused by shifts in the number of CAAT repeats in two separate loci, lic1 (Weiser et al., 1989, Cell 59:657) and lic2 (High et al., 1993, Molec. Microbiol. 9:1275). Shifts allowing the expression of the lic2 gene are correlated with the expression of an epitope with the structure Galα1→4Galβ1→. Since the lic2 gene is homologous to lgtB and lgtE the galactosyl transferases which link Galβ1→4 to respectively Glc or GlcNAc, it is likely that this is its function in *Haemophilus influenzae* LOS synthesis. It is remarkable that while both these mucosal pathogens have evolved frame shift mechanisms to cause antigenic variation of the LOS, that the gonococcal homologs of lic2, (lgtB and lgtE) are not the ones that contain poly-G tracts.

While the frame-shift mechanisms discussed above are suited for on/off regulation of gene expression, the structure of the locus also lends itself to more subtle regulation of the level of expression of the genes. It has been demonstrated that growth rate affects the molecular weight distribution and antigenic character LOS species produced (Morse et at., 1983, Infect. Immun. 41:74). While I have not determined the size of the RNA transcripts it is very likely that lgtA, lgtB and lgtC (in the instance where the poly-G tracts are such that the coding frame is maintained) are transcribed together. The termination codon of lgtA and the initiation codon of lgtB in fact overlap, and the distance between the TAA of lgtB and the ATG of lgtC is only 11 bp. Similarly, the stop codon of lgtD and the start codon of lgtE are separated by only 18 bp. Yet the organization is such that if any of the three genes subject to phase variation are in the off configuration, transcription is able to reinitiate effectively at the beginning of the next gene. This ability to reinitiate transcription was clearly seen with the mutations constructed in this study.

The correlation of LOS structure with function is still in its early stages. The major advances in the field have been the development of an understanding of the structure of the molecules and the ability to relate this, often unambiguously, to the reactivity with a number of well-characterized monoclonal antibodies. Added to this is the realization that in the in vivo environment, which provides CMP-NANA, the organism may or may not sialylate the LOS, depending whether the LOS synthesized is a competent acceptor structure. It is well known that sialylation induces a serum-resistant state in many strains. However, the effect of sialylation in local infection is not as well studied. Van Putten has shown that sialylation of LOS has a marked inhibitory effect on epithelial cell invasion, without apparently greatly altering adhesion (Van Putten, 1993, EMBO J. 12:4043). His studies suggest that in the mucosal infection, LOS structures that cannot be sialylated may be important for efficient cell invasion. In the context of this report, such structures could be achieved either by the efficient addition of the terminal GalNAc or by shortening the LOS chain by silencing the GlcNAc transferase. The correlation of LOS chemistry with biological reaction has been complicated by the leakiness of the existing LOS mutants isolated by pyocin selection (Dudas and Apicella, 1988, Infect. Immun. 56:499; Sandlin et al., 1993, Infect. Immun. 61:3360). This is in fact exemplified with mutant 1291e which shows in addition to the major low molecular weight band, an additional higher band (see FIG. 7). The new insight provided into the genetics of the biosynthesis of gonococcal LOS will allow construction of mutants that are not leaky. For instance, Δ4 and Δ5 should be stable mutants since they no longer contain genes with poly-G tracts. The expression of the genes containing the poly-G tracts could be stabilized by engineering the areas so that glycines are encoded by other codons.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims. It is also to be understood that all base pair sizes given for nucleotides are approximate and are used for the purpose of description. Various references are cited herein, the disclosures of which are incorporated by reference herein in their entirety.

What is claimed is:

1. A method for preparing an oligosaccharide having the structure Galα1→4Galβ1→4Glc, which comprises sequentially performing the steps of:
   a) contacting a reaction mixture comprising an activated Gal to an acceptor moiety comprising a Glc residue in the presence of a glycosyltransferase having an amino acid sequence of SEQ ID NO:6; and
   b) contacting a reaction mixture comprising an activated Gal to the acceptor moiety comprising Galβ→4Glc in the presence of a glycosyltransferase having an amino acid sequence of SEQ ID NO:4.

2. A method for preparing an oligosaccharide having the structure GalNAcβ1→3Galβ1→4GlcNAcβ1→3Galβ1→4Glc, which comprises sequentially performing the steps of:
   a) contacting a reaction mixture comprising an activated Gal to an acceptor moiety comprising a Glc residue in the presence of a glycosyltransferase having an amino acid sequence of SEQ ID NO:6;
   b) contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11;
   c) contacting a reaction mixture comprising an activated Gal to the acceptor moiety comprising a GlcNAcβ1→3Galβ1→4Glc residue in the presence of a glycosyltransferase having an amino acid of SEQ ID NO:8; and
   d) contacting a reaction mixture comprising an activated GalNAc to the acceptor moiety comprising a Galβ1→4GlcNAcβ1→3Galβ1→4Glc residue in the presence of a glycosyltransferase having an amino acid sequence of SEQ ID NO:5 or SEQ ID NO:12.

3. A method for preparing an oligosaccharide having the structure Galβ1→4GlcNAcβ1→3Galβ1→4Glc, which comprises sequentially performing the steps of:
   a) contacting a reaction mixture comprising an activated Gal to an acceptor moiety comprising a Glc residue in the presence of a glycosyltransferase having an amino acid sequence of SEQ ID NO:6;
   b) contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11; and
   c) contacting a reaction mixture comprising an activated Gal to the acceptor moiety comprising a GlcNAcβ1→3Galβ1→4Glc residue in the presence of a glycosyltransferase having an amino acid of SEQ ID NO:8.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 5859 base pairs
        ( B ) TYPE: nucleic acid
        ( C ) STRANDEDNESS: both
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Neisseria gonorrheae
        ( B ) STRAIN: F62

( i x ) FEATURE:
        ( A ) NAME/KEY: CDS
        ( B ) LOCATION: 1..381
        ( D ) OTHER INFORMATION: glys (glycyl tRNA syntetase beta chain)

( i x ) FEATURE:
        ( A ) NAME/KEY: CDS
        ( B ) LOCATION: 445..1491
        ( D ) OTHER INFORMATION: lgtA ( i x ) FEATURE:
        ( A ) NAME/KEY: CDS
        ( B ) LOCATION: 2342..3262
        ( D ) OTHER INFORMATION: lgtC ( i x ) FEATURE:
        ( A ) NAME/KEY: CDS
        ( B ) LOCATION: 3322..4335
        ( D ) OTHER INFORMATION: lgtD ( i x ) FEATURE:
        ( A ) NAME/KEY: CDS
        ( B ) LOCATION: 4354..5196
        ( D ) OTHER INFORMATION: lgtE ( x i ) SEQUENCE DESCRIPTION: SEQ ID NO:1:

```
CTG  CAG  GCC  GTC  GCC  GTA  TTC  AAA  CAA  CTG  CCC  GAA  GCC  GCC  GCG  CTC      48
Leu  Gln  Ala  Val  Ala  Val  Phe  Lys  Gln  Leu  Pro  Glu  Ala  Ala  Ala  Leu
 1                    5                   10                   15

GCC  GCC  GCC  AAC  AAA  CGC  GTG  CAA  AAC  CTG  CTG  AAA  AAA  GCC  GAT  GCC      96
Ala  Ala  Ala  Asn  Lys  Arg  Val  Gln  Asn  Leu  Leu  Lys  Lys  Ala  Asp  Ala
                     20                   25                   30

GCG  TTG  GGC  GAA  GTC  AAT  GAA  AGC  CTG  CTG  CAA  CAG  GAC  GAA  GAA  AAA     144
Ala  Leu  Gly  Glu  Val  Asn  Glu  Ser  Leu  Leu  Gln  Gln  Asp  Glu  Glu  Lys
           35                   40                   45

GCC  CTG  TAC  GCT  GCC  GCG  CAA  GGT  TTG  CAG  CCG  AAA  ATT  GCC  GCC  GCC     192
Ala  Leu  Tyr  Ala  Ala  Ala  Gln  Gly  Leu  Gln  Pro  Lys  Ile  Ala  Ala  Ala
      50                   55                   60

GTC  GCC  GAA  GGC  AAT  TTC  CGA  ACC  GCC  TTG  TCC  GAA  CTG  GCT  TCC  GTC     240
Val  Ala  Glu  Gly  Asn  Phe  Arg  Thr  Ala  Leu  Ser  Glu  Leu  Ala  Ser  Val
 65                   70                   75                   80

AAG  CCG  CAG  GTT  GAT  GCC  TTC  TTC  GAC  GGC  GTG  ATG  GTG  ATG  GCG  GAA     288
Lys  Pro  Gln  Val  Asp  Ala  Phe  Phe  Asp  Gly  Val  Met  Val  Met  Ala  Glu
                     85                   90                   95

GAT  GCC  GCC  GTA  AAA  CAA  AAC  CGC  CTG  AAC  CTG  CTG  AAC  CGC  TTG  GCA     336
Asp  Ala  Ala  Val  Lys  Gln  Asn  Arg  Leu  Asn  Leu  Leu  Asn  Arg  Leu  Ala
                    100                  105                  110
```

```
GAG CAG ATG AAC GCG GTG GCC GAC ATC GCG CTT TTG GGC GAG TAACCGTTGT        388
Glu Gln Met Asn Ala Val Ala Asp Ile Ala Leu Leu Gly Glu
        115                 120                 125

ACAGTCCAAA TGCCGTCTGA AGCCTTCAGG CGGCATCAAA TTATCGGGAG AGTAAA            444

TTG CAG CCT TTA GTC AGC GTA TTG ATT TGC GCC TAC AAC GTA GAA AAA          492
Met Gln Pro Leu Val Ser Val Leu Ile Cys Ala Tyr Asn Val Glu Lys
 1               5                  10                  15

TAT TTT GCC CAA TCA TTA GCC GCC GTC GTG AAT CAG ACT TGG CGC AAC          540
Tyr Phe Ala Gln Ser Leu Ala Ala Val Val Asn Gln Thr Trp Arg Asn
                 20                  25                  30

TTG GAT ATT TTG ATT GTC GAT GAC GGC TCG ACA GAC GGC ACA CTT GCC          588
Leu Asp Ile Leu Ile Val Asp Asp Gly Ser Thr Asp Gly Thr Leu Ala
             35                  40                  45

ATT GCC AAG GAT TTT CAA AAG CGG GAC AGC CGT ATC AAA ATC CTT GCA          636
Ile Ala Lys Asp Phe Gln Lys Arg Asp Ser Arg Ile Lys Ile Leu Ala
         50                  55                  60

CAA GCT CAA AAT TCC GGC CTG ATT CCC TCT TTA AAC ATC GGG CTG GAC          684
Gln Ala Gln Asn Ser Gly Leu Ile Pro Ser Leu Asn Ile Gly Leu Asp
 65                  70                  75                  80

GAA TTG GCA AAG TCG GGG GGG GGG GGG GGG GAA TAT ATT GCG CGC ACC          732
Glu Leu Ala Lys Ser Gly Gly Gly Gly Gly Glu Tyr Ile Ala Arg Thr
                 85                  90                  95

GAT GCC GAC GAT ATT GCC TCC CCC GGC TGG ATT GAG AAA ATC GTG GGC          780
Asp Ala Asp Asp Ile Ala Ser Pro Gly Trp Ile Glu Lys Ile Val Gly
             100                 105                 110

GAG ATG GAA AAA GAC CGC AGC ATC ATT GCG ATG GGC GCG TGG CTG GAA          828
Glu Met Glu Lys Asp Arg Ser Ile Ile Ala Met Gly Ala Trp Leu Glu
         115                 120                 125

GTT TTG TCG GAA GAA AAG GAC GGC AAC CGG CTG GCG CGG CAC CAC AAA          876
Val Leu Ser Glu Glu Lys Asp Gly Asn Arg Leu Ala Arg His His Lys
 130                 135                 140

CAC GGC AAA ATT TGG AAA AAG CCG ACC CGG CAC GAA GAC ATC GCC GCC          924
His Gly Lys Ile Trp Lys Lys Pro Thr Arg His Glu Asp Ile Ala Ala
 145                 150                 155                 160

TTT TTC CCT TTC GGC AAC CCC ATA CAC AAC AAC ACG ATG ATT ATG CGG          972
Phe Phe Pro Phe Gly Asn Pro Ile His Asn Asn Thr Met Ile Met Arg
                 165                 170                 175

CGC AGC GTC ATT GAC GGC GGT TTG CGT TAC GAC ACC GAG CGG GAT TGG         1020
Arg Ser Val Ile Asp Gly Gly Leu Arg Tyr Asp Thr Glu Arg Asp Trp
             180                 185                 190

GCG GAA GAT TAC CAA TTT TGG TAC GAT GTC AGC AAA TTG GGC AGG CTG         1068
Ala Glu Asp Tyr Gln Phe Trp Tyr Asp Val Ser Lys Leu Gly Arg Leu
         195                 200                 205

GCT TAT TAT CCC GAA GCC TTG GTC AAA TAC CGC CTT CAC GCC AAT CAG         1116
Ala Tyr Tyr Pro Glu Ala Leu Val Lys Tyr Arg Leu His Ala Asn Gln
 210                 215                 220

GTT TCA TCC AAA CAC AGC GTC CGC CAA CAC GAA ATC GCG CAA GGC ATC         1164
Val Ser Ser Lys His Ser Val Arg Gln His Glu Ile Ala Gln Gly Ile
 225                 230                 235                 240

CAA AAA ACC GCC AGA AAC GAT TTT TTG CAG TCT ATG GGT TTT AAA ACC         1212
Gln Lys Thr Ala Arg Asn Asp Phe Leu Gln Ser Met Gly Phe Lys Thr
                 245                 250                 255

CGG TTC GAC AGC CTA GAA TAC CGC CAA ACA AAA GCA GCG GCG TAT GAA         1260
Arg Phe Asp Ser Leu Glu Tyr Arg Gln Thr Lys Ala Ala Ala Tyr Glu
             260                 265                 270

CTG CCG GAG AAG GAT TTG CCG GAA GAA GAT TTT GAA CGC GCC CGC CGG         1308
Leu Pro Glu Lys Asp Leu Pro Glu Glu Asp Phe Glu Arg Ala Arg Arg
         275                 280                 285

TTT TTG TAC CAA TGC TTC AAA CGG ACG GAC ACG CCG CCC TCC GGC GCG         1356
```

```
Phe Leu Tyr Gln Cys Phe Lys Arg Thr Asp Thr Pro Pro Ser Gly Ala
    290             295             300

TGG CTG GAT TTC GCG GCA GAC GGC AGG ATG AGG CGG CTG TTT ACC TTG      1404
Trp Leu Asp Phe Ala Ala Asp Gly Arg Met Arg Arg Leu Phe Thr Leu
305             310             315             320

AGG CAA TAC TTC GGC ATT TTG TAC CGG CTG ATT AAA AAC CGC CGG CAG      1452
Arg Gln Tyr Phe Gly Ile Leu Tyr Arg Leu Ile Lys Asn Arg Arg Gln
                325             330             335

GCG CGG TCG GAT TCG GCA GGG AAA GAA CAG GAG ATT TAATGCAAAA           1498
Ala Arg Ser Asp Ser Ala Gly Lys Glu Gln Glu Ile
            340             345

CCACGTTATC AGCTTGGCTT CCGCCGCAGA ACGCAGGGCG CACATTGCCG CAACCTTCGG    1558
CAGTCGCGGC ATCCCGTTCC AGTTTTTCGA CGCACTGATG CCGTCTGAAA GGCTGGAACG    1618
GGCAATGGCG AAACTCGTCC CCGGCTTGTC GGCGCACCCC TATTTGAGCG GAGTGGAAAA    1678
AGCCTGCTTT ATGAGCCACG CCGTATTGTG GAACAGGCA TTGGACGAAG GCGTACCGTA     1738
TATCGCCGTA TTTGAAGATG ATGTCTTACT CGGCGAAGGC GCGGAGCAGT TCCTTGCCGA    1798
AGATACTTGG CTGCAAGAAC GCTTTGACCC CGATTCCGCC TTTGTCGTCC GCTTGGAAAC    1858
GATGTTTATG CACGTCCTGA CCTCGCCCTC CGGCGTGGCG GACTACGGCG GCGCGCCTT     1918
TCCGCTTTTG GAAAGCGAAC ACTGCGGGAC GGCGGGCTAT ATTATTTCCC GAAAGGCGAT    1978
GCGTTTTTTC TTGGACAGGT TTGCCGTTTT GCCGCCCGAA CGCCTGCACC CTGTCGATTT    2038
GATGATGTTC GGCAACCCTG ACGACAGGGA AGGAATGCCG GTTGCCAGC TCAATCCCGC     2098
CTTGTGCGCC CAAGAGCTGC ATTATGCCAA GTTCACGAC CAAAACAGCG CATTGGGCAG     2158
CCTGATCGAA CATGACCGCC GCCTGAACCG CAAACAGCAA TGGCGCGATT CCCCCGCCAA    2218
CACATTCAAA CACCGCCTGA TCCGCGCCTT GACCAAAATC GGCAGGGAAA GGGAAAAACG    2278
CCGGCAAAGG CGCGAACAGT TAATCGGCAA GATTATTGTG CCTTTCCAAT AAAAGGAGAA    2338

AAG ATG GAC ATC GTA TTT GCG GCA GAC GAC AAC TAT GCC GCC TAC CTT     2386
    Met Asp Ile Val Phe Ala Ala Asp Asp Asn Tyr Ala Ala Tyr Leu
    1               5               10              15

TGC GTT GCG GCA AAA AGC GTG GAA GCG GCC CAT CCC GAT ACG GAA ATC      2434
Cys Val Ala Ala Lys Ser Val Glu Ala Ala His Pro Asp Thr Glu Ile
                20              25              30

AGG TTC CAC GTC CTC GAT GCC GGC ATC AGT GAG GAA AAC CGG GCG GCG      2482
Arg Phe His Val Leu Asp Ala Gly Ile Ser Glu Glu Asn Arg Ala Ala
            35              40              45

GTT GCC GCC AAT TTG CGG GGG GGG GGT AAT ATC CGC TTT ATA GAC GTA      2530
Val Ala Ala Asn Leu Arg Gly Gly Gly Asn Ile Arg Phe Ile Asp Val
        50              55              60

AAC CCC GAA GAT TTC GCC GGC TTC CCC TTA AAC ATC AGG CAC ATT TCC      2578
Asn Pro Glu Asp Phe Ala Gly Phe Pro Leu Asn Ile Arg His Ile Ser
65              70              75

ATT ACG ACT TAT GCC CGC CTG AAA TTG GGC GAA TAC ATT GCC GAT TGC      2626
Ile Thr Thr Tyr Ala Arg Leu Lys Leu Gly Glu Tyr Ile Ala Asp Cys
80              85              90              95

GAC AAA GTC CTG TAT CTG GAT ACG GAC GTA TTG GTC AGG GAC GGC CTG      2674
Asp Lys Val Leu Tyr Leu Asp Thr Asp Val Leu Val Arg Asp Gly Leu
                100             105             110

AAG CCC TTA TGG GAT ACC GAT TTG GGC GGT AAC TGG GTC GGC GCG TGC      2722
Lys Pro Leu Trp Asp Thr Asp Leu Gly Gly Asn Trp Val Gly Ala Cys
            115             120             125

ATC GAT TTG TTT GTC GAA AGG CAG GAA GGA TAC AAA CAA AAA ATC GGT      2770
Ile Asp Leu Phe Val Glu Arg Gln Glu Gly Tyr Lys Gln Lys Ile Gly
        130             135             140

ATG GCG GAC GGA GAA TAT TAT TTC AAT GCC GGC GTA TTG CTG ATC AAC      2818
```

```
Met Ala Asp Gly Glu Tyr Tyr Phe Asn Ala Gly Val Leu Leu Ile Asn
145                 150                 155

CTG AAA AAG TGG CGG CGG CAC GAT ATT TTC AAA ATG TCC TGC GAA TGG     2866
Leu Lys Lys Trp Arg Arg His Asp Ile Phe Lys Met Ser Cys Glu Trp
160                 165                 170                 175

GTG GAA CAA TAC AAG GAC GTG ATG CAA TAT CAG GAT CAG GAC ATT TTG     2914
Val Glu Gln Tyr Lys Asp Val Met Gln Tyr Gln Asp Gln Asp Ile Leu
            180                 185                 190

AAC GGG CTG TTT AAA GGC GGG GTG TGT TAT GCG AAC AGC CGT TTC AAC     2962
Asn Gly Leu Phe Lys Gly Gly Val Cys Tyr Ala Asn Ser Arg Phe Asn
        195                 200                 205

TTT ATG CCG ACC AAT TAT GCC TTT ATG GCG AAC GGG TTT GCG TCC CGC     3010
Phe Met Pro Thr Asn Tyr Ala Phe Met Ala Asn Gly Phe Ala Ser Arg
    210                 215                 220

CAT ACC GAC CCG CTT TAC CTC GAC CGT ACC AAT ACG GCG ATG CCC GTC     3058
His Thr Asp Pro Leu Tyr Leu Asp Arg Thr Asn Thr Ala Met Pro Val
225                 230                 235

GCC GTC AGC CAT TAT TGC GGC TCG GCA AAG CCG TGG CAC AGG GAC TGC     3106
Ala Val Ser His Tyr Cys Gly Ser Ala Lys Pro Trp His Arg Asp Cys
240                 245                 250                 255

ACC GTT TGG GGT GCG GAA CGT TTC ACA GAG TTG GCC GGC AGC CTG ACG     3154
Thr Val Trp Gly Ala Glu Arg Phe Thr Glu Leu Ala Gly Ser Leu Thr
            260                 265                 270

ACC GTT CCC GAA GAA TGG CGC GGC AAA CTT GCC GTC CCG CCG ACA AAG     3202
Thr Val Pro Glu Glu Trp Arg Gly Lys Leu Ala Val Pro Pro Thr Lys
        275                 280                 285

TGT ATG CTT CAA AGA TGG CGC AAA AAG CTG TCT GCC AGA TTC TTA CGC     3250
Cys Met Leu Gln Arg Trp Arg Lys Lys Leu Ser Ala Arg Phe Leu Arg
    290                 295                 300

AAG ATT TAT TGACGGGGCA GGCCGTCTGA AGCCTTCAGA CGGCATCGGA             3299
Lys Ile Tyr
305

CGTATCGGAA AGGAGAAACG GA TTG CAG CCT TTA GTC AGC GTA TTG ATT TGC   3351
                        Met Gln Pro Leu Val Ser Val Leu Ile Cys
                         1               5                  10

GCC TAC AAC GCA GAA AAA TAT TTT GCC CAA TCA TTG GCC GCC GTA GTG     3399
Ala Tyr Asn Ala Glu Lys Tyr Phe Ala Gln Ser Leu Ala Ala Val Val
            15                  20                  25

GGG CAG ACT TGG CGC AAC TTG GAT ATT TTG ATT GTC GAT GAC GGC TCG     3447
Gly Gln Thr Trp Arg Asn Leu Asp Ile Leu Ile Val Asp Asp Gly Ser
        30                  35                  40

ACG GAC GGC ACG CCC GCC ATT GCC CGG CAT TTC CAA GAA CAG GAC GGC     3495
Thr Asp Gly Thr Pro Ala Ile Ala Arg His Phe Gln Glu Gln Asp Gly
    45                  50                  55

AGG ATC AGG ATA ATT TCC AAT CCC CGC AAT TTG GGC TTT ATC GCC TCT     3543
Arg Ile Arg Ile Ile Ser Asn Pro Arg Asn Leu Gly Phe Ile Ala Ser
60                  65                  70

TTA AAC ATC GGG CTG GAC GAA TTG GCA AAG TCG GGG GGG GGG GAA TAT     3591
Leu Asn Ile Gly Leu Asp Glu Leu Ala Lys Ser Gly Gly Gly Glu Tyr
75                  80                  85                  90

ATT GCG CGC ACC GAT GCC GAC GAT ATT GCC TCC CCC GGC TGG ATT GAG     3639
Ile Ala Arg Thr Asp Ala Asp Asp Ile Ala Ser Pro Gly Trp Ile Glu
            95                  100                 105

AAA ATC GTG GGC GAG ATG GAA AAA GAC CGC AGC ATC ATT GCG ATG GGC     3687
Lys Ile Val Gly Glu Met Glu Lys Asp Arg Ser Ile Ile Ala Met Gly
        110                 115                 120

GCG TGG TTG GAA GTT TTG TCG GAA GAA AAC AAT AAA AGC GTG CTT GCC     3735
Ala Trp Leu Glu Val Leu Ser Glu Glu Asn Asn Lys Ser Val Leu Ala
    125                 130                 135

GCC ATT GCC CGA AAC GGC GCA ATT TGG GAC AAA CCG ACC CGG CAT GAA     3783
```

|     |     |     |     |     |     |     |     |     |     |     |     |     |     |     |     |
| --- | --- | --- | --- | --- | --- | --- | --- | --- | --- | --- | --- | --- | --- | --- | --- |
| Ala | Ile | Ala | Arg | Asn | Gly | Ala | Ile | Trp | Asp | Lys | Pro | Thr | Arg | His | Glu |
|     | 140 |     |     |     | 145 |     |     |     |     | 150 |     |     |     |     |     |

| GAC | ATT | GTC | GCC | GTT | TTC | CCT | TTC | GGC | AAC | CCC | ATA | CAC | AAC | AAC | ACG | 3831 |
| --- | --- | --- | --- | --- | --- | --- | --- | --- | --- | --- | --- | --- | --- | --- | --- | --- |
| Asp | Ile | Val | Ala | Val | Phe | Pro | Phe | Gly | Asn | Pro | Ile | His | Asn | Asn | Thr |     |
| 155 |     |     |     |     | 160 |     |     |     |     | 165 |     |     |     |     | 170 |     |

| ATG | ATT | ATG | AGG | CGC | AGC | GTC | ATT | GAC | GGC | GGT | TTG | CGG | TTC | GAT | CCA | 3879 |
| Met | Ile | Met | Arg | Arg | Ser | Val | Ile | Asp | Gly | Gly | Leu | Arg | Phe | Asp | Pro |     |
|     |     |     |     | 175 |     |     |     |     | 180 |     |     |     |     | 185 |     |     |

| GCC | TAT | ATC | CAC | GCC | GAA | GAC | TAT | AAG | TTT | TGG | TAC | GAA | GCC | GGC | AAA | 3927 |
| Ala | Tyr | Ile | His | Ala | Glu | Asp | Tyr | Lys | Phe | Trp | Tyr | Glu | Ala | Gly | Lys |     |
|     |     |     | 190 |     |     |     |     | 195 |     |     |     |     | 200 |     |     |     |

| CTG | GGC | AGG | CTG | GCT | TAT | TAT | CCC | GAA | GCC | TTG | GTC | AAA | TAC | CGC | TTC | 3975 |
| Leu | Gly | Arg | Leu | Ala | Tyr | Tyr | Pro | Glu | Ala | Leu | Val | Lys | Tyr | Arg | Phe |     |
|     |     | 205 |     |     |     |     | 210 |     |     |     |     | 215 |     |     |     |     |

| CAT | CAA | GAC | CAG | ACT | TCT | TCC | AAA | TAC | AAC | CTG | CAA | CAG | CGC | AGG | ACG | 4023 |
| His | Gln | Asp | Gln | Thr | Ser | Ser | Lys | Tyr | Asn | Leu | Gln | Gln | Arg | Arg | Thr |     |
|     | 220 |     |     |     |     | 225 |     |     |     |     | 230 |     |     |     |     |     |

| GCG | TGG | AAA | ATC | AAA | GAA | GAA | ATC | AGG | GCG | GGG | TAT | TGG | AAG | GCG | GCA | 4071 |
| Ala | Trp | Lys | Ile | Lys | Glu | Glu | Ile | Arg | Ala | Gly | Tyr | Trp | Lys | Ala | Ala |     |
| 235 |     |     |     |     | 240 |     |     |     |     | 245 |     |     |     |     | 250 |     |

| GGC | ATA | GCC | GTC | GGG | GCG | GAC | TGC | CTG | AAT | TAC | GGG | CTT | TTG | AAA | TCA | 4119 |
| Gly | Ile | Ala | Val | Gly | Ala | Asp | Cys | Leu | Asn | Tyr | Gly | Leu | Leu | Lys | Ser |     |
|     |     |     |     | 255 |     |     |     |     | 260 |     |     |     |     | 265 |     |     |

| ACG | GCA | TAT | GCG | TTG | TAC | GAA | AAA | GCC | TTG | TCC | GGA | CAG | GAT | ATC | GGA | 4167 |
| Thr | Ala | Tyr | Ala | Leu | Tyr | Glu | Lys | Ala | Leu | Ser | Gly | Gln | Asp | Ile | Gly |     |
|     |     | 270 |     |     |     |     | 275 |     |     |     |     | 280 |     |     |     |     |

| TGC | CTC | CGC | CTG | TTC | CTG | TAC | GAA | TAT | TTC | TTG | TCG | TTG | GAA | AAG | TAT | 4215 |
| Cys | Leu | Arg | Leu | Phe | Leu | Tyr | Glu | Tyr | Phe | Leu | Ser | Leu | Glu | Lys | Tyr |     |
|     |     | 285 |     |     |     |     | 290 |     |     |     |     | 295 |     |     |     |     |

| TCT | TTG | ACC | GAT | TTG | CTG | GAT | TTC | TTG | ACA | GAC | CGC | GTG | ATG | AGG | AAG | 4263 |
| Ser | Leu | Thr | Asp | Leu | Leu | Asp | Phe | Leu | Thr | Asp | Arg | Val | Met | Arg | Lys |     |
|     |     | 300 |     |     |     |     | 305 |     |     |     |     | 310 |     |     |     |     |

| CTG | TTT | GCC | GCA | CCG | CAA | TAT | AGG | AAA | ATC | CTG | AAA | AAA | ATG | TTA | CGC | 4311 |
| Leu | Phe | Ala | Ala | Pro | Gln | Tyr | Arg | Lys | Ile | Leu | Lys | Lys | Met | Leu | Arg |     |
| 315 |     |     |     |     | 320 |     |     |     |     | 325 |     |     |     |     | 330 |     |

| CCT | TGG | AAA | TAC | CGC | AGC | TAT | TGAAACCGAA | CAGGATAAAT | C | ATG | CAA | AAC | 4362 |
| Pro | Trp | Lys | Tyr | Arg | Ser | Tyr |     |     |     | Met | Gln | Asn |     |
|     |     |     |     | 335 |     |     |     |     |     | 1   |     |     |     |

| CAC | GTT | ATC | AGC | TTG | GCT | TCC | GCC | GCA | GAG | CGC | AGG | GCG | CAC | ATT | GCC | 4410 |
| His | Val | Ile | Ser | Leu | Ala | Ser | Ala | Ala | Glu | Arg | Arg | Ala | His | Ile | Ala |     |
|     |     | 5   |     |     |     |     | 10  |     |     |     |     | 15  |     |     |     |     |

| GAT | ACC | TTC | GGC | AGT | CGC | GGC | ATC | CCG | TTC | CAG | TTT | TTC | GAC | GCA | CTG | 4458 |
| Asp | Thr | Phe | Gly | Ser | Arg | Gly | Ile | Pro | Phe | Gln | Phe | Phe | Asp | Ala | Leu |     |
| 20  |     |     |     |     | 25  |     |     |     |     | 30  |     |     |     |     | 35  |     |

| ATG | CCG | TCT | GAA | AGG | CTG | GAA | CAG | GCG | ATG | GCG | GAA | CTC | GTC | CCC | GGC | 4506 |
| Met | Pro | Ser | Glu | Arg | Leu | Glu | Gln | Ala | Met | Ala | Glu | Leu | Val | Pro | Gly |     |
|     |     |     |     | 40  |     |     |     |     | 45  |     |     |     |     | 50  |     |     |

| TTG | TCG | GCG | CAC | CCC | TAT | TTG | AGC | GGA | GTG | GAA | AAA | GCC | TGC | TTT | ATG | 4554 |
| Leu | Ser | Ala | His | Pro | Tyr | Leu | Ser | Gly | Val | Glu | Lys | Ala | Cys | Phe | Met |     |
|     |     |     | 55  |     |     |     |     | 60  |     |     |     |     | 65  |     |     |     |

| AGC | CAC | GCC | GTA | TTG | TGG | GAA | CAG | GCG | TTG | GAT | GAA | GGT | CTG | CCG | TAT | 4602 |
| Ser | His | Ala | Val | Leu | Trp | Glu | Gln | Ala | Leu | Asp | Glu | Gly | Leu | Pro | Tyr |     |
|     |     | 70  |     |     |     |     | 75  |     |     |     |     | 80  |     |     |     |     |

| ATC | GCC | GTA | TTT | GAG | GAC | GAC | GTT | TTA | CTC | GGC | GAA | GGC | GCG | GAG | CAG | 4650 |
| Ile | Ala | Val | Phe | Glu | Asp | Asp | Val | Leu | Leu | Gly | Glu | Gly | Ala | Glu | Gln |     |
|     | 85  |     |     |     |     | 90  |     |     |     |     | 95  |     |     |     |     |     |

| TTC | CTT | GCC | GAA | GAT | ACT | TGG | TTG | GAA | GAG | CGT | TTT | GAC | AAG | GAT | TCC | 4698 |
| Phe | Leu | Ala | Glu | Asp | Thr | Trp | Leu | Glu | Glu | Arg | Phe | Asp | Lys | Asp | Ser |     |
| 100 |     |     |     |     | 105 |     |     |     |     | 110 |     |     |     |     | 115 |     |

| GCC | TTT | ATC | GTC | CGT | TTG | GAA | ACG | ATG | TTT | GCG | AAA | GTT | ATT | GTC | AGA | 4746 |

```
                Ala Phe Ile Val Arg Leu Glu Thr Met Phe Ala Lys Val Ile Val Arg
                                120                 125                 130

CCG GAT AAA GTC CTG AAT TAT GAA AAC CGG TCA TTT CCT TTG CTG GAG                4794
Pro Asp Lys Val Leu Asn Tyr Glu Asn Arg Ser Phe Pro Leu Leu Glu
                135                 140                 145

AGC GAA CAT TGT GGG ACG GCT GGC TAT ATC ATT TCG CGT GAG GCG ATG                4842
Ser Glu His Cys Gly Thr Ala Gly Tyr Ile Ile Ser Arg Glu Ala Met
            150                 155                 160

CGG TTT TTC TTG GAC AGG TTT GCC GTT TTG CCG CCA GAG CGG ATT AAA                4890
Arg Phe Phe Leu Asp Arg Phe Ala Val Leu Pro Pro Glu Arg Ile Lys
        165                 170                 175

GCG GTA GAT TTG ATG ATG TTT ACT TAT TTC TTT GAT AAG GAG GGG ATG                4938
Ala Val Asp Leu Met Met Phe Thr Tyr Phe Phe Asp Lys Glu Gly Met
180                 185                 190                 195

CCT GTT TAT CAG GTT AGT CCC GCC TTA TGT ACC CAA GAA TTG CAT TAT                4986
Pro Val Tyr Gln Val Ser Pro Ala Leu Cys Thr Gln Glu Leu His Tyr
                200                 205                 210

GCC AAG TTT CTC AGT CAA AAC AGT ATG TTG GGT AGC GAT TTG GAA AAA                5034
Ala Lys Phe Leu Ser Gln Asn Ser Met Leu Gly Ser Asp Leu Glu Lys
            215                 220                 225

GAT AGG GAA CAA GGA AGA AGA CAC CGC CGT TCG TTG AAG GTG ATG TTT                5082
Asp Arg Glu Gln Gly Arg Arg His Arg Arg Ser Leu Lys Val Met Phe
        230                 235                 240

GAC TTG AAG CGT GCT TTG GGT AAA TTC GGT AGG GAA AAG AAG AAA AGA                5130
Asp Leu Lys Arg Ala Leu Gly Lys Phe Gly Arg Glu Lys Lys Lys Arg
    245                 250                 255

ATG GAG CGT CAA AGG CAG GCG GAG CTT GAG AAA GTT TAC GGC AGG CGG                5178
Met Glu Arg Gln Arg Gln Ala Glu Leu Glu Lys Val Tyr Gly Arg Arg
260                 265                 270                 275

GTC ATA TTG TTC AAA TAGTTTGTGT AAAATATAGG GGATTAAAAT CAGAAATGGA                5233
Val Ile Leu Phe Lys
                280

CACACTGTCA TTCCCGCGCA GGCGGGAATC TAGGTCTTTA AACTTCGGTT TTTTCCGATA             5293

AATTCTTGCC GCATTAAAAT TCCAGATTCC CGCTTTCGCG GGATGACGG  CGGGGGGATT             5353

GTTGCTTTTT CGGATAAAAT CCCGTGTTTT TTCATCTGCT AGGTAAAATC GCCCCAAAGC             5413

GTCTGCATCG CGGCGATGGC GGCGAGTGGG GCGGTTTCTG TGCGTAAAAT CCGTTTTCCG             5473

AGTGTAACCG CCTGAAAGCC GGCTTCAAAT GCCTGTTGTT CTTCCTGTTC TGTCCAGCCG             5533

CCTTCGGGCC CGACCATAAA GACGATTGCG CCGGACGGGT GGCGGATGTC GCCGAGTTTG             5593

CAGGCGCGGT TGATGCTCAT AATCAGCTTG GTGTTTCAG ACGGCATTTT GTCGAGTGCT              5653

TCACGGTAGC CGATGATGGG CAGTACGGGG GGAACGGTGT TCCTGCCGCT TTGTTCGCAC             5713

GCGGAGATGA CGATTTCCTG CCAGCGTGCG AGGCGTTTGG CGGCGCGTTC TCCGTCGAGG             5773

CGGACGATGC AGCGTTCGCT GATGACGGGC TGTATGGCGG TTACGCCGAG TTCGACGCTT             5833

TTTTGCAGGG TGAAATCCAT GCGATC                                                  5859
```

(2) INFORMATION FOR SEQ ID NO:2:

(i) SEQUENCE CHARACTERISTICS:
       (A) LENGTH: 126 amino acids
       (B) TYPE: amino acid
       (D) TOPOLOGY: linear (ii) MOLECULE TYPE: protein (xi) SEQUENCE DESCRIPTION: SEQ ID NO:2:

```
Leu Gln Ala Val Ala Val Phe Lys Gln Leu Pro Glu Ala Ala Ala Leu
 1               5                  10                  15
```

| Ala | Ala | Ala | Asn | Lys | Arg | Val | Gln | Asn | Leu | Leu | Lys | Lys | Ala | Asp | Ala |
|---|---|---|---|---|---|---|---|---|---|---|---|---|---|---|---|
| | | | 20 | | | | | 25 | | | | | 30 | | |

| Ala | Leu | Gly | Glu | Val | Asn | Glu | Ser | Leu | Leu | Gln | Gln | Asp | Glu | Glu | Lys |
|---|---|---|---|---|---|---|---|---|---|---|---|---|---|---|---|
| | | 35 | | | | | 40 | | | | | 45 | | | |

| Ala | Leu | Tyr | Ala | Ala | Ala | Gln | Gly | Leu | Gln | Pro | Lys | Ile | Ala | Ala | Ala |
|---|---|---|---|---|---|---|---|---|---|---|---|---|---|---|---|
| | | 50 | | | | 55 | | | | | 60 | | | | |

| Val | Ala | Glu | Gly | Asn | Phe | Arg | Thr | Ala | Leu | Ser | Glu | Leu | Ala | Ser | Val |
|---|---|---|---|---|---|---|---|---|---|---|---|---|---|---|---|
| 65 | | | | | 70 | | | | | 75 | | | | | 80 |

| Lys | Pro | Gln | Val | Asp | Ala | Phe | Phe | Asp | Gly | Val | Met | Val | Met | Ala | Glu |
|---|---|---|---|---|---|---|---|---|---|---|---|---|---|---|---|
| | | | | 85 | | | | | 90 | | | | | 95 | |

| Asp | Ala | Ala | Val | Lys | Gln | Asn | Arg | Leu | Asn | Leu | Leu | Asn | Arg | Leu | Ala |
|---|---|---|---|---|---|---|---|---|---|---|---|---|---|---|---|
| | | | 100 | | | | | 105 | | | | | 110 | | |

| Glu | Gln | Met | Asn | Ala | Val | Ala | Asp | Ile | Ala | Leu | Leu | Gly | Glu | | |
|---|---|---|---|---|---|---|---|---|---|---|---|---|---|---|---|
| | | 115 | | | | | 120 | | | | | 125 | | | |

( 2 ) INFORMATION FOR SEQ ID NO:3:

( i ) SEQUENCE CHARACTERISTICS:
  ( A ) LENGTH: 348 amino acids
  ( B ) TYPE: amino acid
  ( D ) TOPOLOGY: linear ( i i ) MOLECULE TYPE: protein ( x i ) SEQUENCE DESCRIPTION: SEQ ID NO:3:

| Met | Gln | Pro | Leu | Val | Ser | Val | Leu | Ile | Cys | Ala | Tyr | Asn | Val | Glu | Lys |
|---|---|---|---|---|---|---|---|---|---|---|---|---|---|---|---|
| 1 | | | | 5 | | | | | 10 | | | | | 15 | |

| Tyr | Phe | Ala | Gln | Ser | Leu | Ala | Ala | Val | Val | Asn | Gln | Thr | Trp | Arg | Asn |
|---|---|---|---|---|---|---|---|---|---|---|---|---|---|---|---|
| | | | 20 | | | | | 25 | | | | | 30 | | |

| Leu | Asp | Ile | Leu | Ile | Val | Asp | Asp | Gly | Ser | Thr | Asp | Gly | Thr | Leu | Ala |
|---|---|---|---|---|---|---|---|---|---|---|---|---|---|---|---|
| | | | 35 | | | | | 40 | | | | | 45 | | |

| Ile | Ala | Lys | Asp | Phe | Gln | Lys | Arg | Asp | Ser | Arg | Ile | Lys | Ile | Leu | Ala |
|---|---|---|---|---|---|---|---|---|---|---|---|---|---|---|---|
| | | 50 | | | | | 55 | | | | | 60 | | | |

| Gln | Ala | Gln | Asn | Ser | Gly | Leu | Ile | Pro | Ser | Leu | Asn | Ile | Gly | Leu | Asp |
|---|---|---|---|---|---|---|---|---|---|---|---|---|---|---|---|
| 65 | | | | | 70 | | | | | 75 | | | | | 80 |

| Glu | Leu | Ala | Lys | Ser | Gly | Gly | Gly | Gly | Glu | Tyr | Ile | Ala | Arg | Thr |
|---|---|---|---|---|---|---|---|---|---|---|---|---|---|---|
| | | | | 85 | | | | | 90 | | | | | 95 |

| Asp | Ala | Asp | Asp | Ile | Ala | Ser | Pro | Gly | Trp | Ile | Glu | Lys | Ile | Val | Gly |
|---|---|---|---|---|---|---|---|---|---|---|---|---|---|---|---|
| | | | 100 | | | | | 105 | | | | | 110 | | |

| Glu | Met | Glu | Lys | Asp | Arg | Ser | Ile | Ile | Ala | Met | Gly | Ala | Trp | Leu | Glu |
|---|---|---|---|---|---|---|---|---|---|---|---|---|---|---|---|
| | | 115 | | | | | 120 | | | | | 125 | | | |

| Val | Leu | Ser | Glu | Glu | Lys | Asp | Gly | Asn | Arg | Leu | Ala | Arg | His | His | Lys |
|---|---|---|---|---|---|---|---|---|---|---|---|---|---|---|---|
| | 130 | | | | | 135 | | | | | 140 | | | | |

| His | Gly | Lys | Ile | Trp | Lys | Lys | Pro | Thr | Arg | His | Glu | Asp | Ile | Ala | Ala |
|---|---|---|---|---|---|---|---|---|---|---|---|---|---|---|---|
| 145 | | | | | 150 | | | | | 155 | | | | | 160 |

| Phe | Phe | Pro | Phe | Gly | Asn | Pro | Ile | His | Asn | Asn | Thr | Met | Ile | Met | Arg |
|---|---|---|---|---|---|---|---|---|---|---|---|---|---|---|---|
| | | | | 165 | | | | | 170 | | | | | 175 | |

| Arg | Ser | Val | Ile | Asp | Gly | Gly | Leu | Arg | Tyr | Asp | Thr | Glu | Arg | Asp | Trp |
|---|---|---|---|---|---|---|---|---|---|---|---|---|---|---|---|
| | | | 180 | | | | | 185 | | | | | 190 | | |

| Ala | Glu | Asp | Tyr | Gln | Phe | Trp | Tyr | Asp | Val | Ser | Lys | Leu | Gly | Arg | Leu |
|---|---|---|---|---|---|---|---|---|---|---|---|---|---|---|---|
| | | 195 | | | | | 200 | | | | | 205 | | | |

| Ala | Tyr | Tyr | Pro | Glu | Ala | Leu | Val | Lys | Tyr | Arg | Leu | His | Ala | Asn | Gln |
|---|---|---|---|---|---|---|---|---|---|---|---|---|---|---|---|
| | 210 | | | | | 215 | | | | | 220 | | | | |

| Val | Ser | Ser | Lys | His | Ser | Val | Arg | Gln | His | Glu | Ile | Ala | Gln | Gly | Ile |
|---|---|---|---|---|---|---|---|---|---|---|---|---|---|---|---|
| 225 | | | | | 230 | | | | | 235 | | | | | 240 |

| Gln | Lys | Thr | Ala | Arg | Asn | Asp | Phe | Leu | Gln | Ser | Met | Gly | Phe | Lys | Thr |
|---|---|---|---|---|---|---|---|---|---|---|---|---|---|---|---|
| | | | | 245 | | | | | 250 | | | | | 255 | |

| Arg | Phe | Asp | Ser     | Leu | Glu | Tyr | Arg     | Thr | Lys | Ala | Ala     | Ala | Tyr | Glu |
|     |     |     | 260     |     |     |     | 265     |     |     |     | 270     |     |     |     |

| Leu | Pro | Glu | Lys     | Asp | Leu | Pro | Glu     | Glu | Asp | Phe | Glu     | Arg | Ala | Arg | Arg |
|     |     |     | 275     |     |     |     | 280     |     |     |     | 285     |     |     |     |     |

| Phe | Leu | Tyr | Gln     | Cys | Phe | Lys | Arg     | Thr | Asp | Thr | Pro     | Pro | Ser | Gly | Ala |
|     |     |     | 290     |     |     |     | 295     |     |     |     | 300     |     |     |     |     |

| Trp | Leu | Asp | Phe     | Ala | Ala | Asp | Gly     | Arg | Met | Arg | Arg     | Leu | Phe | Thr | Leu |
| 305 |     |     |         |     | 310 |     |         |     |     | 315 |         |     |     |     | 320 |

| Arg | Gln | Tyr | Phe     | Gly | Ile | Leu | Tyr     | Arg | Leu | Ile | Lys     | Asn | Arg | Arg | Gln |
|     |     |     | 325     |     |     |     | 330     |     |     |     |         |     |     | 335 |     |

| Ala | Arg | Ser | Asp     | Ser | Ala | Gly | Lys     | Glu | Gln | Glu | Ile     |
|     |     |     | 340     |     |     |     |         |     |     |     |         |
|     |     |     |         |     |     |     | 345     |     |     |     |         |

( 2 ) INFORMATION FOR SEQ ID NO:4:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asp | Ile | Val     | Phe | Ala | Ala | Asp     | Asp | Asn | Tyr | Ala     | Ala | Tyr | Leu | Cys |
| 1   |     |     |         | 5   |     |     |         |     | 10  |     |         |     |     | 15  |     |

| Val | Ala | Ala | Lys     | Ser | Val | Glu | Ala     | Ala | His | Pro | Asp     | Thr | Glu | Ile | Arg |
|     |     |     | 20      |     |     |     | 25      |     |     |     |         |     | 30  |     |     |

| Phe | His | Val | Leu     | Asp | Ala | Gly | Ile     | Ser | Glu | Glu | Asn     | Arg | Ala | Ala | Val |
|     |     |     | 35      |     |     |     | 40      |     |     |     |         |     | 45  |     |     |

| Ala | Ala | Asn | Leu     | Arg | Gly | Gly | Gly     | Asn | Ile | Arg | Phe     | Ile | Asp | Val | Asn |
|     |     | 50  |         |     |     |     | 55      |     |     |     |         | 60  |     |     |     |

| Pro | Glu | Asp | Phe     | Ala | Gly | Phe | Pro     | Leu | Asn | Ile | Arg     | His | Ile | Ser | Ile |
| 65  |     |     |         |     | 70  |     |         |     |     | 75  |         |     |     |     | 80  |

| Thr | Thr | Tyr | Ala     | Arg | Leu | Lys | Leu     | Gly | Glu | Tyr | Ile     | Ala | Asp | Cys | Asp |
|     |     |     |         | 85  |     |     |         |     | 90  |     |         |     |     | 95  |     |

| Lys | Val | Leu | Tyr     | Leu | Asp | Thr | Asp     | Val | Leu | Val | Arg     | Asp | Gly | Leu | Lys |
|     |     |     | 100     |     |     |     | 105     |     |     |     |         |     | 110 |     |     |

| Pro | Leu | Trp | Asp     | Thr | Asp | Leu | Gly     | Gly | Asn | Trp | Val     | Gly | Ala | Cys | Ile |
|     |     |     | 115     |     |     |     | 120     |     |     |     |         | 125 |     |     |     |

| Asp | Leu | Phe | Val     | Glu | Arg | Gln | Glu     | Gly | Tyr | Lys | Gln     | Lys | Ile | Gly | Met |
|     | 130 |     |         |     |     |     | 135     |     |     |     | 140     |     |     |     |     |

| Ala | Asp | Gly | Glu     | Tyr | Tyr | Phe | Asn     | Ala | Gly | Val | Leu     | Leu | Ile | Asn | Leu |
| 145 |     |     |         |     | 150 |     |         |     |     | 155 |         |     |     |     | 160 |

| Lys | Lys | Trp | Arg     | Arg | His | Asp | Ile     | Phe | Lys | Met | Ser     | Cys | Glu | Trp | Val |
|     |     |     | 165     |     |     |     |         |     | 170 |     |         |     |     | 175 |     |

| Glu | Gln | Tyr | Lys     | Asp | Val | Met | Gln     | Tyr | Gln | Asp | Gln     | Asp | Ile | Leu | Asn |
|     |     |     | 180     |     |     |     |         | 185 |     |     |         |     | 190 |     |     |

| Gly | Leu | Phe | Lys     | Gly | Gly | Val | Cys     | Tyr | Ala | Asn | Ser     | Arg | Phe | Asn | Phe |
|     |     |     | 195     |     |     |     | 200     |     |     |     |         | 205 |     |     |     |

| Met | Pro | Thr | Asn     | Tyr | Ala | Phe | Met     | Ala | Asn | Gly | Phe     | Ala | Ser | Arg | His |
|     | 210 |     |         |     |     | 215 |         |     |     |     | 220     |     |     |     |     |

| Thr | Asp | Pro | Leu     | Tyr | Leu | Asp | Arg     | Thr | Asn | Thr | Ala     | Met | Pro | Val | Ala |
| 225 |     |     |         |     | 230 |     |         |     |     | 235 |         |     |     |     | 240 |

| Val | Ser | His | Tyr     | Cys | Gly | Ser | Ala     | Lys | Pro | Trp | His     | Arg | Asp | Cys | Thr |
|     |     |     |         | 245 |     |     |         |     | 250 |     |         |     |     | 255 |     |

| Val | Trp | Gly | Ala     | Glu | Arg | Phe | Thr     | Glu | Leu | Ala | Gly     | Ser | Leu | Thr | Thr |

|     |     |     |     | 260 |     |     |     |     | 265 |     |     |     |     | 270 |
|-----|-----|-----|-----|-----|-----|-----|-----|-----|-----|-----|-----|-----|-----|-----|

Val Pro Glu Glu Trp Arg Gly Lys Leu Ala Val Pro Pro Thr Lys Cys
        275                        280                         285

Met Leu Gln Arg Trp Arg Lys Lys Leu Ser Ala Arg Phe Leu Arg Lys
        290                        295                         300

Ile Tyr
305

( 2 ) INFORMATION FOR SEQ ID NO:5:

( i ) SEQUENCE CHARACTERISTICS:
        ( A ) LENGTH: 337 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Met Gln Pro Leu Val Ser Val Leu Ile Cys Ala Tyr Asn Ala Glu Lys
1                  5                    10                      15

Tyr Phe Ala Gln Ser Leu Ala Ala Val Val Gly Gln Thr Trp Arg Asn
        20                        25                         30

Leu Asp Ile Leu Ile Val Asp Asp Gly Ser Thr Asp Gly Thr Pro Ala
            35                    40                    45

Ile Ala Arg His Phe Gln Glu Gln Asp Gly Arg Ile Arg Ile Ile Ser
        50                        55                      60

Asn Pro Arg Asn Leu Gly Phe Ile Ala Ser Leu Asn Ile Gly Leu Asp
65                 70                    75                  80

Glu Leu Ala Lys Ser Gly Gly Glu Tyr Ile Ala Arg Thr Asp Ala
                85                  90                  95

Asp Asp Ile Ala Ser Pro Gly Trp Ile Glu Lys Ile Val Gly Glu Met
            100                    105                110

Glu Lys Asp Arg Ser Ile Ile Ala Met Gly Ala Trp Leu Glu Val Leu
        115                    120                125

Ser Glu Glu Asn Asn Lys Ser Val Leu Ala Ala Ile Ala Arg Asn Gly
    130                    135                140

Ala Ile Trp Asp Lys Pro Thr Arg His Glu Asp Ile Val Ala Val Phe
145                150                    155              160

Pro Phe Gly Asn Pro Ile His Asn Asn Thr Met Ile Met Arg Arg Ser
                165                    170            175

Val Ile Asp Gly Gly Leu Arg Phe Asp Pro Ala Tyr Ile His Ala Glu
        180                    185                190

Asp Tyr Lys Phe Trp Tyr Glu Ala Gly Lys Leu Gly Arg Leu Ala Tyr
            195                  200                205

Tyr Pro Glu Ala Leu Val Lys Tyr Arg Phe His Gln Asp Gln Thr Ser
    210                    215                220

Ser Lys Tyr Asn Leu Gln Gln Arg Arg Thr Ala Trp Lys Ile Lys Glu
225                230                    235              240

Glu Ile Arg Ala Gly Tyr Trp Lys Ala Ala Gly Ile Ala Val Gly Ala
                245                    250            255

Asp Cys Leu Asn Tyr Gly Leu Leu Lys Ser Thr Ala Tyr Ala Leu Tyr
            260                    265                270

Glu Lys Ala Leu Ser Gly Gln Asp Ile Gly Cys Leu Arg Leu Phe Leu
        275                    280                285

Tyr Glu Tyr Phe Leu Ser Leu Glu Lys Tyr Ser Leu Thr Asp Leu Leu
    290                    295                300

-continued

```
Asp Phe Leu Thr Asp Arg Val Met Arg Lys Leu Phe Ala Ala Pro Gln
305                 310                 315                 320

Tyr Arg Lys Ile Leu Lys Lys Met Leu Arg Pro Trp Lys Tyr Arg Ser
                325                 330                 335

Tyr
```

( 2 ) INFORMATION FOR SEQ ID NO:6:

( i ) SEQUENCE CHARACTERISTICS:
        ( A ) LENGTH: 280 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gln Asn His Val Ile Ser Leu Ala Ser Ala Ala Glu Arg Arg Ala
1               5                   10                  15

His Ile Ala Asp Thr Phe Gly Ser Arg Gly Ile Pro Phe Gln Phe Phe
                20                  25                  30

Asp Ala Leu Met Pro Ser Glu Arg Leu Glu Gln Ala Met Ala Glu Leu
                35                  40                  45

Val Pro Gly Leu Ser Ala His Pro Tyr Leu Ser Gly Val Glu Lys Ala
        50                  55                  60

Cys Phe Met Ser His Ala Val Leu Trp Glu Gln Ala Leu Asp Glu Gly
65                  70                  75                  80

Leu Pro Tyr Ile Ala Val Phe Glu Asp Val Leu Leu Gly Glu Gly
            85                  90                  95

Ala Glu Gln Phe Leu Ala Glu Asp Thr Trp Leu Glu Glu Arg Phe Asp
                100                 105                 110

Lys Asp Ser Ala Phe Ile Val Arg Leu Glu Thr Met Phe Ala Lys Val
            115                 120                 125

Ile Val Arg Pro Asp Lys Val Leu Asn Tyr Glu Asn Arg Ser Phe Pro
        130                 135                 140

Leu Leu Glu Ser Glu His Cys Gly Thr Ala Gly Tyr Ile Ile Ser Arg
145                 150                 155                 160

Glu Ala Met Arg Phe Phe Leu Asp Arg Phe Ala Val Leu Pro Pro Glu
                165                 170                 175

Arg Ile Lys Ala Val Asp Leu Met Met Phe Thr Tyr Phe Asp Lys
            180                 185                 190

Glu Gly Met Pro Val Tyr Gln Val Ser Pro Ala Leu Cys Thr Gln Glu
        195                 200                 205

Leu His Tyr Ala Lys Phe Leu Ser Gln Asn Ser Met Leu Gly Ser Asp
    210                 215                 220

Leu Glu Lys Asp Arg Glu Gln Gly Arg Arg His Arg Arg Ser Leu Lys
225                 230                 235                 240

Val Met Phe Asp Leu Lys Arg Ala Leu Gly Lys Phe Gly Arg Glu Lys
            245                 250                 255

Lys Lys Arg Met Glu Arg Gln Arg Gln Ala Glu Leu Glu Lys Val Tyr
            260                 265                 270

Gly Arg Arg Val Ile Leu Phe Lys
    275                 280
```

( 2 ) INFORMATION FOR SEQ ID NO:7:

( i ) SEQUENCE CHARACTERISTICS:
        ( A ) LENGTH: 5859 base pairs
        ( B ) TYPE: nucleic acid ( C ) STRANDEDNESS: both
( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Neisseria gonorrheae
( B ) STRAIN: F62

( i x ) FEATURE:
( A ) NAME/KEY: CDS
( B ) LOCATION: 1491..2330
( D ) OTHER INFORMATION: lgtB ( x i ) SEQUENCE DESCRIPTION: SEQ ID NO:7:

```
CTGCAGGCCG  TCGCCGTATT  CAAACAACTG  CCCGAAGCCG  CCGCGCTCGC  CGCCGCCAAC        60

AAACGCGTGC  AAAACCTGCT  GAAAAAGCC   GATGCCGCGT  TGGGCGAAGT  CAATGAAAGC       120

CTGCTGCAAC  AGGACGAAGA  AAAAGCCCTG  TACGCTGCCG  CGCAAGGTTT  GCAGCCGAAA       180

ATTGCCGCCG  CCGTCGCCGA  AGGCAATTTC  CGAACCGCCT  TGTCCGAACT  GGCTTCCGTC       240

AAGCCGCAGG  TTGATGCCTT  CTTCGACGGC  GTGATGGTGA  TGGCGGAAGA  TGCCGCCGTA       300

AAACAAAACC  GCCTGAACCT  GCTGAACCGC  TTGGCAGAGC  AGATGAACGC  GGTGGCCGAC       360

ATCGCGCTTT  TGGGCGAGTA  ACCGTTGTAC  AGTCCAAATG  CCGTCTGAAG  CCTTCAGGCG       420

GCATCAAATT  ATCGGGAGAG  TAAATTGCAG  CCTTTAGTCA  GCGTATTGAT  TTGCGCCTAC       480

AACGTAGAAA  AATATTTTGC  CCAATCATTA  GCCGCCGTCG  TGAATCAGAC  TTGGCGCAAC       540

TTGGATATTT  TGATTGTCGA  TGACGGCTCG  ACAGACGGCA  CACTTGCCAT  TGCCAAGGAT       600

TTTCAAAAGC  GGGACAGCCG  TATCAAAATC  CTTGCACAAG  CTCAAAATTC  CGGCCTGATT       660

CCCTCTTTAA  ACATCGGGCT  GGACGAATTG  GCAAAGTCGG  GGGGGGGGGG  GGGGGAATAT       720

ATTGCGCGCA  CCGATGCCGA  CGATATTGCC  TCCCCCGGCT  GGATTGAGAA  AATCGTGGGC       780

GAGATGGAAA  AAGACCGCAG  CATCATTGCG  ATGGGCGCGT  GGCTGGAAGT  TTTGTCGGAA       840

GAAAAGGACG  GCAACCGGCT  GGCGCGGCAC  CACAAACACG  GCAAAATTTG  GAAAAAGCCG       900

ACCCGGCACG  AAGACATCGC  CGCCTTTTTC  CCTTTCGGCA  ACCCCATACA  CAACAACACG       960

ATGATTATGC  GGCGCAGCGT  CATTGACGGC  GGTTTGCGTT  ACGACACCGA  GCGGGATTGG      1020

GCGGAAGATT  ACCAATTTTG  GTACGATGTC  AGCAAATTGG  GCAGGCTGGC  TTATTATCCC      1080

GAAGCCTTGG  TCAAATACCG  CCTTCACGCC  AATCAGGTTT  CATCCAAACA  CAGCGTCCGC      1140

CAACACGAAA  TCGCGCAAGG  CATCCAAAAA  ACCGCCAGAA  ACGATTTTTT  GCAGTCTATG      1200

GGTTTTAAAA  CCCGGTTCGA  CAGCCTAGAA  TACCGCCAAA  CAAAAGCAGC  GGCGTATGAA      1260

CTGCCGGAGA  AGGATTTGCC  GGAAGAAGAT  TTTGAACGCG  CCCGCCGGTT  TTTGTACCAA      1320

TGCTTCAAAC  GGACGGACAC  GCCGCCCTCC  GGCGCGTGGC  TGGATTTCGC  GGCAGACGGC      1380

AGGATGAGGC  GGCTGTTTAC  CTTGAGGCAA  TACTTCGGCA  TTTTGTACCG  GCTGATTAAA      1440

AACCGCCGGC  AGGCGCGGTC  GGATTCGGCA  GGGAAAGAAC  AGGAGATTTA  ATG CAA         1496
                                                           Met Gln
                                                           1

AAC CAC GTT ATC AGC TTG GCT TCC GCC GCA GAA CGC AGG GCG CAC ATT           1544
Asn His Val Ile Ser Leu Ala Ser Ala Ala Glu Arg Arg Ala His Ile
        5                10                   15

GCC GCA ACC TTC GGC AGT CGC GGC ATC CCG TTC CAG TTT TTC GAC GCA           1592
Ala Ala Thr Phe Gly Ser Arg Gly Ile Pro Phe Gln Phe Phe Asp Ala
    20                  25                  30
```

-continued

| | | | | | | | | | | | | | | | | |
|---|---|---|---|---|---|---|---|---|---|---|---|---|---|---|---|---|
| CTG | ATG | CCG | TCT | GAA | AGG | CTG | GAA | CGG | GCA | ATG | GCG | GAA | CTC | GTC | CCC | 1640 |
| Leu | Met | Pro | Ser | Glu | Arg | Leu | Glu | Arg | Ala | Met | Ala | Glu | Leu | Val | Pro | |
| 35 | | | | 40 | | | | | 45 | | | | | 50 | | |
| GGC | TTG | TCG | GCG | CAC | CCC | TAT | TTG | AGC | GGA | GTG | GAA | AAA | GCC | TGC | TTT | 1688 |
| Gly | Leu | Ser | Ala | His | Pro | Tyr | Leu | Ser | Gly | Val | Glu | Lys | Ala | Cys | Phe | |
| | | | | 55 | | | | 60 | | | | | 65 | | | |
| ATG | AGC | CAC | GCC | GTA | TTG | TGG | GAA | CAG | GCA | TTG | GAC | GAA | GGC | GTA | CCG | 1736 |
| Met | Ser | His | Ala | Val | Leu | Trp | Glu | Gln | Ala | Leu | Asp | Glu | Gly | Val | Pro | |
| | | | 70 | | | | 75 | | | | | 80 | | | | |
| TAT | ATC | GCC | GTA | TTT | GAA | GAT | GAT | GTC | TTA | CTC | GGC | GAA | GGC | GCG | GAG | 1784 |
| Tyr | Ile | Ala | Val | Phe | Glu | Asp | Asp | Val | Leu | Leu | Gly | Glu | Gly | Ala | Glu | |
| | | 85 | | | | | 90 | | | | | 95 | | | | |
| CAG | TTC | CTT | GCC | GAA | GAT | ACT | TGG | CTG | CAA | GAA | CGC | TTT | GAC | CCC | GAT | 1832 |
| Gln | Phe | Leu | Ala | Glu | Asp | Thr | Trp | Leu | Gln | Glu | Arg | Phe | Asp | Pro | Asp | |
| | 100 | | | | | 105 | | | | | 110 | | | | | |
| TCC | GCC | TTT | GTC | GTC | CGC | TTG | GAA | ACG | ATG | TTT | ATG | CAC | GTC | CTG | ACC | 1880 |
| Ser | Ala | Phe | Val | Val | Arg | Leu | Glu | Thr | Met | Phe | Met | His | Val | Leu | Thr | |
| 115 | | | | 120 | | | | | 125 | | | | | 130 | | |
| TCG | CCC | TCC | GGC | GTG | GCG | GAC | TAC | GGC | GGG | CGC | GCC | TTT | CCG | CTT | TTG | 1928 |
| Ser | Pro | Ser | Gly | Val | Ala | Asp | Tyr | Gly | Gly | Arg | Ala | Phe | Pro | Leu | Leu | |
| | | | | 135 | | | | 140 | | | | | 145 | | | |
| GAA | AGC | GAA | CAC | TGC | GGG | ACG | GCG | GGC | TAT | ATT | ATT | TCC | CGA | AAG | GCG | 1976 |
| Glu | Ser | Glu | His | Cys | Gly | Thr | Ala | Gly | Tyr | Ile | Ile | Ser | Arg | Lys | Ala | |
| | | | 150 | | | | 155 | | | | | 160 | | | | |
| ATG | CGT | TTT | TTC | TTG | GAC | AGG | TTT | GCC | GTT | TTG | CCG | CCC | GAA | CGC | CTG | 2024 |
| Met | Arg | Phe | Phe | Leu | Asp | Arg | Phe | Ala | Val | Leu | Pro | Pro | Glu | Arg | Leu | |
| | | 165 | | | | 170 | | | | | 175 | | | | | |
| CAC | CCT | GTC | GAT | TTG | ATG | ATG | TTC | GGC | AAC | CCT | GAC | GAC | AGG | GAA | GGA | 2072 |
| His | Pro | Val | Asp | Leu | Met | Met | Phe | Gly | Asn | Pro | Asp | Asp | Arg | Glu | Gly | |
| | 180 | | | | | 185 | | | | | 190 | | | | | |
| ATG | CCG | GTT | TGC | CAG | CTC | AAT | CCC | GCC | TTG | TGC | GCC | CAA | GAG | CTG | CAT | 2120 |
| Met | Pro | Val | Cys | Gln | Leu | Asn | Pro | Ala | Leu | Cys | Ala | Gln | Glu | Leu | His | |
| 195 | | | | 200 | | | | | 205 | | | | | 210 | | |
| TAT | GCC | AAG | TTT | CAC | GAC | CAA | AAC | AGC | GCA | TTG | GGC | AGC | CTG | ATC | GAA | 2168 |
| Tyr | Ala | Lys | Phe | His | Asp | Gln | Asn | Ser | Ala | Leu | Gly | Ser | Leu | Ile | Glu | |
| | | | | 215 | | | | 220 | | | | | 225 | | | |
| CAT | GAC | CGC | CGC | CTG | AAC | CGC | AAA | CAG | CAA | TGG | CGC | GAT | TCC | CCC | GCC | 2216 |
| His | Asp | Arg | Arg | Leu | Asn | Arg | Lys | Gln | Gln | Trp | Arg | Asp | Ser | Pro | Ala | |
| | | | 230 | | | | 235 | | | | | 240 | | | | |
| AAC | ACA | TTC | AAA | CAC | CGC | CTG | ATC | CGC | GCC | TTG | ACC | AAA | ATC | GGC | AGG | 2264 |
| Asn | Thr | Phe | Lys | His | Arg | Leu | Ile | Arg | Ala | Leu | Thr | Lys | Ile | Gly | Arg | |
| | | | 245 | | | | 250 | | | | | 255 | | | | |
| GAA | AGG | GAA | AAA | CGC | CGG | CAA | AGG | CGC | GAA | CAG | TTA | ATC | GGC | AAG | ATT | 2312 |
| Glu | Arg | Glu | Lys | Arg | Arg | Gln | Arg | Arg | Glu | Gln | Leu | Ile | Gly | Lys | Ile | |
| | 260 | | | | | 265 | | | | | 270 | | | | | |
| ATT | GTG | CCT | TTC | CAA | TAAAAGGAGA | | AAAGATGGAC | | ATCGTATTTG | | CGGCAGACGA | | | | | 2367 |
| Ile | Val | Pro | Phe | Gln | | | | | | | | | | | | |
| 275 | | | | 280 | | | | | | | | | | | | |

| | | | | |
|---|---|---|---|---|
| CAACTATGCC | GCCTACCTTT | GCGTTGCGGC | AAAAAGCGTG | GAAGCGGCCC | ATCCCGATAC | 2427 |
| GGAAATCAGG | TTCCACGTCC | TCGATGCCGG | CATCAGTGAG | GAAAACCGGG | CGGCGGTTGC | 2487 |
| CGCCAATTTG | CGGGGGGGGG | GTAATATCCG | CTTTATAGAC | GTAAACCCCG | AAGATTTCGC | 2547 |
| CGGCTTCCCC | TTAAACATCA | GGCACATTTC | CATTACGACT | TATGCCCGCC | TGAAATTGGG | 2607 |
| CGAATACATT | GCCGATTGCG | ACAAAGTCCT | GTATCTGGAT | ACGGACGTAT | TGGTCAGGGA | 2667 |
| CGGCCTGAAG | CCCTTATGGG | ATACCGATTT | GGGCGGTAAC | TGGGTCGGCG | CGTGCATCGA | 2727 |
| TTTGTTTGTC | GAAAGGCAGG | AAGGATACAA | ACAAAAAATC | GGTATGGCGG | ACGGAGAATA | 2787 |
| TTATTTCAAT | GCCGGCGTAT | TGCTGATCAA | CCTGAAAAAG | TGGCGGCGGC | ACGATATTTT | 2847 |

-continued

| | | | | | |
|---|---|---|---|---|---|
| CAAAATGTCC | TGCGAATGGG | TGGAACAATA | CAAGGACGTG | ATGCAATATC | AGGATCAGGA | 2907 |
| CATTTTGAAC | GGGCTGTTTA | AAGGCGGGGT | GTGTTATGCG | AACAGCCGTT | TCAACTTTAT | 2967 |
| GCCGACCAAT | TATGCCTTTA | TGGCGAACGG | GTTTGCGTCC | CGCCATACCG | ACCCGCTTTA | 3027 |
| CCTCGACCGT | ACCAATACGG | CGATGCCCGT | CGCCGTCAGC | CATTATTGCG | GCTCGGCAAA | 3087 |
| GCCGTGGCAC | AGGGACTGCA | CCGTTTGGGG | TGCGGAACGT | TTCACAGAGT | TGGCCGGCAG | 3147 |
| CCTGACGACC | GTTCCCGAAG | AATGGCGCGG | CAAACTTGCC | GTCCGCCGA | CAAAGTGTAT | 3207 |
| GCTTCAAAGA | TGGCGCAAAA | AGCTGTCTGC | CAGATTCTTA | CGCAAGATTT | ATTGACGGGG | 3267 |
| CAGGCCGTCT | GAAGCCTTCA | GACGGCATCG | GACGTATCGG | AAAGGAGAAA | CGGATTGCAG | 3327 |
| CCTTTAGTCA | GCGTATTGAT | TTGCGCCTAC | AACGCAGAAA | AATATTTTGC | CCAATCATTG | 3387 |
| GCCGCCGTAG | TGGGCAGAC | TTGGCGCAAC | TTGGATATTT | TGATTGTCGA | TGACGGCTCG | 3447 |
| ACGGACGGCA | CGCCCGCCAT | TGCCCGGCAT | TTCCAAGAAC | AGGACGGCAG | GATCAGGATA | 3507 |
| ATTTCCAATC | CCCGCAATTT | GGGCTTTATC | GCCTCTTTAA | ACATCGGGCT | GGACGAATTG | 3567 |
| GCAAAGTCGG | GGGGGGGGA | ATATATTGCG | CGCACCGATG | CCGACGATAT | TGCCTCCCCC | 3627 |
| GGCTGGATTG | AGAAAATCGT | GGGCGAGATG | GAAAAGACC | GCAGCATCAT | TGCGATGGGC | 3687 |
| GCGTGGTTGG | AAGTTTTGTC | GGAAGAAAAC | AATAAAAGCG | TGCTTGCCGC | CATTGCCCGA | 3747 |
| AACGGCGCAA | TTTGGGACAA | ACCGACCCGG | CATGAAGACA | TTGTCGCCGT | TTTCCCTTTC | 3807 |
| GGCAACCCCA | TACACAACAA | CACGATGATT | ATGAGGCGCA | GCGTCATTGA | CGGCGGTTTG | 3867 |
| CGGTTCGATC | CAGCCTATAT | CCACGCCGAA | GACTATAAGT | TTTGGTACGA | AGCCGGCAAA | 3927 |
| CTGGGCAGGC | TGGCTTATTA | TCCCGAAGCC | TTGGTCAAAT | ACCGCTTCCA | TCAAGACCAG | 3987 |
| ACTTCTTCCA | AATACAACCT | GCAACAGCGC | AGGACGGCGT | GGAAAATCAA | GAAGAAATC | 4047 |
| AGGGCGGGGT | ATTGGAAGGC | GGCAGGCATA | GCCGTCGGGG | CGGACTGCCT | GAATTACGGG | 4107 |
| CTTTTGAAAT | CAACGGCATA | TGCGTTGTAC | GAAAAAGCCT | TGTCCGGACA | GGATATCGGA | 4167 |
| TGCCTCCGCC | TGTTCCTGTA | CGAATATTTC | TTGTCGTTGG | AAAAGTATTC | TTTGACCGAT | 4227 |
| TTGCTGGATT | TCTTGACAGA | CCGCGTGATG | AGGAAGCTGT | TGCCGCACC | GCAATATAGG | 4287 |
| AAAATCCTGA | AAAAAATGTT | ACGCCCTTGG | AAATACCGCA | GCTATTGAAA | CCGAACAGGA | 4347 |
| TAAATCATGC | AAAACCACGT | TATCAGCTTG | GCTTCCGCCG | CAGAGCGCAG | GGCGCACATT | 4407 |
| GCCGATACCT | TCGGCAGTCG | CGGCATCCCG | TTCCAGTTTT | TCGACGCACT | GATGCCGTCT | 4467 |
| GAAAGGCTGG | AACAGGCGAT | GGCGGAACTC | GTCCCGGCT | TGTCGGCGCA | CCCCTATTTG | 4527 |
| AGCGGAGTGG | AAAAAGCCTG | CTTTATGAGC | CACGCCGTAT | TGTGGGAACA | GGCGTTGGAT | 4587 |
| GAAGGTCTGC | CGTATATCGC | CGTATTTGAG | GACGACGTTT | TACTCGGCGA | AGGCGCGGAG | 4647 |
| CAGTTCCTTG | CCGAAGATAC | TTGGTTGGAA | GAGCGTTTTG | ACAAGGATTC | CGCCTTTATC | 4707 |
| GTCCGTTTGG | AAACGATGTT | TGCGAAAGTT | ATTGTCAGAC | CGGATAAAGT | CCTGAATTAT | 4767 |
| GAAAACCGGT | CATTTCCTTT | GCTGGAGAGC | GAACATTGTG | GGACGGCTGG | CTATATCATT | 4827 |
| TCGCGTGAGG | CGATGCGGTT | TTTCTTGGAC | AGGTTGCCG | TTTGCCGCC | AGAGCGGATT | 4887 |
| AAAGCGGTAG | ATTTGATGAT | GTTTACTTAT | TTCTTTGATA | AGGAGGGGAT | GCCTGTTTAT | 4947 |
| CAGGTTAGTC | CCGCCTTATG | TACCCAAGAA | TTGCATTATG | CCAAGTTTCT | CAGTCAAAAC | 5007 |
| AGTATGTTGG | GTAGCGATTT | GGAAAAAGAT | AGGGAACAAG | GAAGAAGACA | CCGCCGTTCG | 5067 |
| TTGAAGGTGA | TGTTTGACTT | GAAGCGTGCT | TTGGGTAAAT | TCGGTAGGGA | AAAGAAGAAA | 5127 |
| AGAATGGAGC | GTCAAAGGCA | GGCGGAGCTT | GAGAAAGTTT | ACGGCAGGCG | GGTCATATTG | 5187 |
| TTCAAATAGT | TTGTGTAAAA | TATAGGGGAT | TAAAATCAGA | AATGGACACA | CTGTCATTCC | 5247 |

| | | | | |
|---|---|---|---|---|
| CGCGCAGGCG | GGAATCTAGG | TCTTTAAACT | TCGGTTTTTT | CCGATAAATT CTTGCCGCAT | 5307 |
| TAAAATTCCA | GATTCCCGCT | TTCGCGGGGA | TGACGGCGGG | GGGATTGTTG CTTTTTCGGA | 5367 |
| TAAAATCCCG | TGTTTTTTCA | TCTGCTAGGT | AAAATCGCCC | CAAAGCGTCT GCATCGCGGC | 5427 |
| GATGGCGGCG | AGTGGGGCGG | TTTCTGTGCG | TAAAATCCGT | TTTCCGAGTG TAACCGCCTG | 5487 |
| AAAGCCGGCT | TCAAATGCCT | GTTGTTCTTC | CTGTTCTGTC | CAGCCGCCTT CGGGCCCGAC | 5547 |
| CATAAAGACG | ATTGCGCCGG | ACGGGTGGCG | GATGTCGCCG | AGTTTGCAGG CGCGGTTGAT | 5607 |
| GCTCATAATC | AGCTTGGTGT | TTTCAGACGG | CATTTGTCG | AGTGCTTCAC GGTAGCCGAT | 5667 |
| GATGGGCAGT | ACGGGGGGAA | CGGTGTTCCT | GCCGCTTTGT | TCGCACGCGG AGATGACGAT | 5727 |
| TTCCTGCCAG | CGTGCGAGGC | GTTTGGCGGC | GCGTTCTCCG | TCGAGGCGGA CGATGCAGCG | 5787 |
| TTCGCTGATG | ACGGGCTGTA | TGGCGGTTAC | GCCGAGTTCG | ACGCTTTTTT GCAGGGTGAA | 5847 |
| ATCCATGCGA | TC | | | | 5859 |

( 2 ) INFORMATION FOR SEQ ID NO:8:

( i ) SEQUENCE CHARACTERISTICS:
( A ) LENGTH: 279 amino acids
( B ) TYPE: amino acid
( D ) TOPOLOGY: linear ( i i ) MOLECULE TYPE: protein ( x i ) SEQUENCE DESCRIPTION: SEQ ID NO:8:

| Met | Gln | Asn | His | Val | Ile | Ser | Leu | Ala | Ser | Ala | Glu | Arg | Arg | Ala |
|---|---|---|---|---|---|---|---|---|---|---|---|---|---|---|
| 1 | | | | 5 | | | | | 10 | | | | | 15 |

| His | Ile | Ala | Ala | Thr | Phe | Gly | Ser | Arg | Gly | Ile | Pro | Phe | Gln | Phe | Phe |
|---|---|---|---|---|---|---|---|---|---|---|---|---|---|---|---|
| | | | | 20 | | | | | 25 | | | | | 30 | |

| Asp | Ala | Leu | Met | Pro | Ser | Glu | Arg | Leu | Glu | Arg | Ala | Met | Ala | Glu | Leu |
|---|---|---|---|---|---|---|---|---|---|---|---|---|---|---|---|
| | | | 35 | | | | | 40 | | | | | 45 | | |

| Val | Pro | Gly | Leu | Ser | Ala | His | Pro | Tyr | Leu | Ser | Gly | Val | Glu | Lys | Ala |
|---|---|---|---|---|---|---|---|---|---|---|---|---|---|---|---|
| | 50 | | | | | 55 | | | | | 60 | | | | |

| Cys | Phe | Met | Ser | His | Ala | Val | Leu | Trp | Glu | Gln | Ala | Leu | Asp | Glu | Gly |
|---|---|---|---|---|---|---|---|---|---|---|---|---|---|---|---|
| 65 | | | | | 70 | | | | | 75 | | | | | 80 |

| Val | Pro | Tyr | Ile | Ala | Val | Phe | Glu | Asp | Asp | Val | Leu | Leu | Gly | Glu | Gly |
|---|---|---|---|---|---|---|---|---|---|---|---|---|---|---|---|
| | | | | 85 | | | | | 90 | | | | | 95 | |

| Ala | Glu | Gln | Phe | Leu | Ala | Glu | Asp | Thr | Trp | Leu | Gln | Glu | Arg | Phe | Asp |
|---|---|---|---|---|---|---|---|---|---|---|---|---|---|---|---|
| | | | 100 | | | | | 105 | | | | | 110 | | |

| Pro | Asp | Ser | Ala | Phe | Val | Val | Arg | Leu | Glu | Thr | Met | Phe | Met | His | Val |
|---|---|---|---|---|---|---|---|---|---|---|---|---|---|---|---|
| | | 115 | | | | | 120 | | | | | 125 | | | |

| Leu | Thr | Ser | Pro | Ser | Gly | Val | Ala | Asp | Tyr | Gly | Gly | Arg | Ala | Phe | Pro |
|---|---|---|---|---|---|---|---|---|---|---|---|---|---|---|---|
| | 130 | | | | | 135 | | | | | 140 | | | | |

| Leu | Leu | Glu | Ser | Glu | His | Cys | Gly | Thr | Ala | Gly | Tyr | Ile | Ile | Ser | Arg |
|---|---|---|---|---|---|---|---|---|---|---|---|---|---|---|---|
| 145 | | | | | 150 | | | | | 155 | | | | | 160 |

| Lys | Ala | Met | Arg | Phe | Phe | Leu | Asp | Arg | Phe | Ala | Val | Leu | Pro | Pro | Glu |
|---|---|---|---|---|---|---|---|---|---|---|---|---|---|---|---|
| | | | | 165 | | | | | 170 | | | | | 175 | |

| Arg | Leu | His | Pro | Val | Asp | Leu | Met | Met | Phe | Gly | Asn | Pro | Asp | Asp | Arg |
|---|---|---|---|---|---|---|---|---|---|---|---|---|---|---|---|
| | | | 180 | | | | | 185 | | | | | 190 | | |

| Glu | Gly | Met | Pro | Val | Cys | Gln | Leu | Asn | Pro | Ala | Leu | Cys | Ala | Gln | Glu |
|---|---|---|---|---|---|---|---|---|---|---|---|---|---|---|---|
| | | 195 | | | | | 200 | | | | | 205 | | | |

| Leu | His | Tyr | Ala | Lys | Phe | His | Asp | Gln | Asn | Ser | Ala | Leu | Gly | Ser | Leu |
|---|---|---|---|---|---|---|---|---|---|---|---|---|---|---|---|
| | 210 | | | | | 215 | | | | | 220 | | | | |

| Ile | Glu | His | Asp | Arg | Arg | Leu | Asn | Arg | Lys | Gln | Gln | Trp | Arg | Asp | Ser |
|---|---|---|---|---|---|---|---|---|---|---|---|---|---|---|---|
| 225 | | | | | 230 | | | | | 235 | | | | | 240 |

| Pro | Ala | Asn | Thr | Phe | Lys | His | Arg | Leu | Ile | Arg | Ala | Leu | Thr | Lys | Ile |

```
                    245                         250                         255
Gly  Arg  Glu  Arg  Glu  Lys  Arg  Arg  Gln  Arg  Arg  Glu  Gln  Leu  Ile  Gly
               260                         265                         270
Lys  Ile  Ile  Val  Pro  Phe  Gln
               275
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: PCR primer ( x i ) SEQUENCE DESCRIPTION: SEQ ID NO:9:

```
GCCGAGAAAA CTATTGGTGG A                                                21
```

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: PCR primer ( x i ) SEQUENCE DESCRIPTION: SEQ ID NO:10:

```
AAAACATGCA GGAATTGACG AT                                               22
```

( 2 ) INFORMATION FOR SEQ ID NO:11:

( i ) SEQUENCE CHARACTERISTICS:
        ( A ) LENGTH: 348 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Leu  Gln  Pro  Leu  Val  Ser  Val  Leu  Ile  Cys  Ala  Tyr  Asn  Val  Glu  Lys
 1                   5                        10                         15
Tyr  Phe  Ala  Gln  Ser  Leu  Ala  Ala  Val  Val  Asn  Gln  Thr  Trp  Arg  Asn
               20                        25                         30
Leu  Asp  Ile  Leu  Ile  Val  Asp  Asp  Gly  Ser  Thr  Asp  Gly  Thr  Leu  Ala
               35                        40                         45
Ile  Ala  Lys  Asp  Phe  Gln  Lys  Arg  Asp  Ser  Arg  Ile  Lys  Ile  Leu  Ala
               50                        55                         60
Gln  Ala  Gln  Asn  Ser  Gly  Leu  Ile  Pro  Ser  Leu  Asn  Ile  Gly  Leu  Asp
65                        70                        75                         80
Glu  Leu  Ala  Lys  Ser  Gly  Gly  Gly  Gly  Glu  Tyr  Ile  Ala  Arg  Thr
```

```
                              85                    90                    95

Asp Ala Asp Asp Ile Ala Ser Pro Gly Trp Ile Glu Lys Ile Val Gly
            100                 105                 110

Glu Met Glu Lys Asp Arg Ser Ile Ile Ala Met Gly Ala Trp Leu Glu
        115                 120                 125

Val Leu Ser Glu Glu Lys Asp Gly Asn Arg Leu Ala Arg His His Lys
    130                 135                 140

His Gly Lys Ile Trp Lys Lys Pro Thr Arg His Glu Asp Ile Ala Ala
145                     150                 155                 160

Phe Phe Pro Phe Gly Asn Pro Ile His Asn Asn Thr Met Ile Met Arg
                165                 170                 175

Arg Ser Val Ile Asp Gly Gly Leu Arg Tyr Asp Thr Glu Arg Asp Trp
            180                 185                 190

Ala Glu Asp Tyr Gln Phe Trp Tyr Asp Val Ser Lys Leu Gly Arg Leu
        195                 200                 205

Ala Tyr Tyr Pro Glu Ala Leu Val Lys Tyr Arg Leu His Ala Asn Gln
    210                 215                 220

Val Ser Ser Lys His Ser Val Arg Gln His Glu Ile Ala Gln Gly Ile
225                     230                 235                 240

Gln Lys Thr Ala Arg Asn Asp Phe Leu Gln Ser Met Gly Phe Lys Thr
                245                 250                 255

Arg Phe Asp Ser Leu Glu Tyr Arg Gln Thr Lys Ala Ala Ala Tyr Glu
            260                 265                 270

Leu Pro Glu Lys Asp Leu Pro Glu Glu Asp Phe Glu Arg Ala Arg Arg
        275                 280                 285

Phe Leu Tyr Gln Cys Phe Lys Arg Thr Asp Thr Pro Pro Ser Gly Ala
    290                 295                 300

Trp Leu Asp Phe Ala Ala Asp Gly Arg Met Arg Arg Leu Phe Thr Leu
305                     310                 315                 320

Arg Gln Tyr Phe Gly Ile Leu Tyr Arg Leu Ile Lys Asn Arg Arg Gln
                325                 330                 335

Ala Arg Ser Asp Ser Ala Gly Lys Glu Gln Glu Ile
            340                 345
```

( 2 ) INFORMATION FOR SEQ ID NO:12:

( i ) SEQUENCE CHARACTERISTICS:
( A ) LENGTH: 337 amino acids
( B ) TYPE: amino acid
( D ) TOPOLOGY: linear ( i i ) MOLECULE TYPE: protein ( x i ) SEQUENCE DESCRIPTION: SEQ ID NO:12:

```
Leu Gln Pro Leu Val Ser Val Leu Ile Cys Ala Tyr Asn Ala Glu Lys
1               5                   10                  15

Tyr Phe Ala Gln Ser Leu Ala Ala Val Val Gly Gln Thr Trp Arg Asn
            20                  25                  30

Leu Asp Ile Leu Ile Val Asp Asp Gly Ser Thr Asp Gly Thr Pro Ala
        35                  40                  45

Ile Ala Arg His Phe Gln Glu Gln Asp Gly Arg Ile Arg Ile Ile Ser
    50                  55                  60

Asn Pro Arg Asn Leu Gly Phe Ile Ala Ser Leu Asn Ile Gly Leu Asp
65                  70                  75                  80

Glu Leu Ala Lys Ser Gly Gly Gly Glu Tyr Ile Ala Arg Thr Asp Ala
                85                  90                  95
```

-continued

| | | | | | | | | | | | | | | |
|---|---|---|---|---|---|---|---|---|---|---|---|---|---|---|
| Asp | Asp | Ile | Ala | Ser | Pro | Gly | Trp | Ile | Glu | Lys | Ile | Val | Gly | Glu | Met |
| | | | 100 | | | | | 105 | | | | | 110 | | |
| Glu | Lys | Asp | Arg | Ser | Ile | Ile | Ala | Met | Gly | Ala | Trp | Leu | Glu | Val | Leu |
| | | 115 | | | | | 120 | | | | | 125 | | | |
| Ser | Glu | Glu | Asn | Asn | Lys | Ser | Val | Leu | Ala | Ala | Ile | Ala | Arg | Asn | Gly |
| | 130 | | | | | 135 | | | | | 140 | | | | |
| Ala | Ile | Trp | Asp | Lys | Pro | Thr | Arg | His | Glu | Asp | Ile | Val | Ala | Val | Phe |
| 145 | | | | | 150 | | | | | 155 | | | | | 160 |
| Pro | Phe | Gly | Asn | Pro | Ile | His | Asn | Asn | Thr | Met | Ile | Met | Arg | Arg | Ser |
| | | | | 165 | | | | | 170 | | | | | 175 | |
| Val | Ile | Asp | Gly | Gly | Leu | Arg | Phe | Asp | Pro | Ala | Tyr | Ile | His | Ala | Glu |
| | | | 180 | | | | | 185 | | | | | 190 | | |
| Asp | Tyr | Lys | Phe | Trp | Tyr | Glu | Ala | Gly | Lys | Leu | Gly | Arg | Leu | Ala | Tyr |
| | | 195 | | | | | 200 | | | | | 205 | | | |
| Tyr | Pro | Glu | Ala | Leu | Val | Lys | Tyr | Arg | Phe | His | Gln | Asp | Gln | Thr | Ser |
| | 210 | | | | | 215 | | | | | 220 | | | | |
| Ser | Lys | Tyr | Asn | Leu | Gln | Gln | Arg | Arg | Thr | Ala | Trp | Lys | Ile | Lys | Glu |
| 225 | | | | | 230 | | | | | 235 | | | | | 240 |
| Glu | Ile | Arg | Ala | Gly | Tyr | Trp | Lys | Ala | Ala | Gly | Ile | Ala | Val | Gly | Ala |
| | | | | 245 | | | | | 250 | | | | | 255 | |
| Asp | Cys | Leu | Asn | Tyr | Gly | Leu | Leu | Lys | Ser | Thr | Ala | Tyr | Ala | Leu | Tyr |
| | | | 260 | | | | | 265 | | | | | 270 | | |
| Glu | Lys | Ala | Leu | Ser | Gly | Gln | Asp | Ile | Gly | Cys | Leu | Arg | Leu | Phe | Leu |
| | | 275 | | | | | 280 | | | | | 285 | | | |
| Tyr | Glu | Tyr | Phe | Leu | Ser | Leu | Glu | Lys | Tyr | Ser | Leu | Thr | Asp | Leu | Leu |
| | 290 | | | | | 295 | | | | | 300 | | | | |
| Asp | Phe | Leu | Thr | Asp | Arg | Val | Met | Arg | Lys | Leu | Phe | Ala | Ala | Pro | Gln |
| 305 | | | | | 310 | | | | | 315 | | | | | 320 |
| Tyr | Arg | Lys | Ile | Leu | Lys | Lys | Met | Leu | Arg | Pro | Trp | Lys | Tyr | Arg | Ser |
| | | | | 325 | | | | | 330 | | | | | 335 | |
| Tyr | | | | | | | | | | | | | | | |